United States Patent [19]

Itoh et al.

[11] Patent Number: 5,380,842
[45] Date of Patent: Jan. 10, 1995

[54] PHTHALOCYANINE COMPOUNDS AND USAGE THEREOF

[75] Inventors: Hisato Itoh, Yokohama; Akio Karasawa, Zushi; Kenichi Sugimoto, Yokohama; Takahisa Oguchi, Yokohama; Shin Aihara, Yokohama, all of Japan

[73] Assignees: Mitsui Toatsu Chemicals, Incorporated, Tokyo; Yamamoto Chemicals, Incorporated, Osaku, both of Japan

[21] Appl. No.: 901,484

[22] Filed: Jun. 22, 1992

[30] Foreign Application Priority Data

Jun. 20, 1991 [JP] Japan .................. 3-148262
Dec. 20, 1991 [JP] Japan .................. 3-338557
Feb. 20, 1992 [JP] Japan .................. 4-033031

[51] Int. Cl.⁶ .................................. C09B 47/04
[52] U.S. Cl. .......................... 540/128; 540/129; 540/139; 540/140
[58] Field of Search ........... 540/128, 129, 135, 140, 540/136, 137; 524/88; 430/78

[56] References Cited

U.S. PATENT DOCUMENTS 2,456,274 12/1948 Gutzwiller ................. 540/140
5,024,926  6/1991 Holm et al. ................ 540/128

FOREIGN PATENT DOCUMENTS 155780  2/1985 European Pat. Off. ..... 540/140
0155780  9/1985 European Pat. Off. .
0186404  7/1986 European Pat. Off. .
0232427  8/1987 European Pat. Off. .
0373643  6/1990 European Pat. Off. .

(List continued on next page.)

OTHER PUBLICATIONS

Miura et al. Chemical Abstracts vol. 105, 1986 Abstract 52262t.
Kuroiwa et al. Chemical Abstracts vol. 106, 1987 Abstract 19999m.
Kuroiwa et al. Chemical Abstracts vol. 106, 1987 Abstract 224565.
Kuroiwa et al. Chemical Abstracts vol. 106, 1987 Abstract 224577p.

(List continued on next page.)

Primary Examiner—Nicholas Rizzo
Assistant Examiner—P. K. Sripada
Attorney, Agent, or Firm—Millen, White, Zelano, & Branigan

[57] ABSTRACT

Phthalocyanine compounds represented by the below-described formula are suitable for use in the fabrication of color filters.

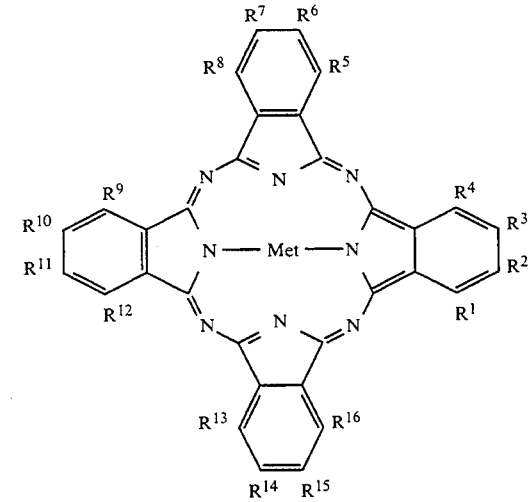

wherein $R^1$, $R^4$, $R^5$, $R^8$, $R^9$, $R^{12}$, $R^{13}$ and $R^{16}$ represent a group represented by the below-described formula, H or a halogen atom, $R^2$, $R^3$, $R^6$, $R^7$, $R^{10}$, $R^{11}$, $R^{14}$ and $R^{15}$ represent an alkyl, alkoxyl, alkylthio, alkylamino, dialkylamino or aryloxyl, arylthio group or —COOR$^{17}$, $R^{17}$ being a particular monovalent group, H or a halogen atom; and Met represents a metal atom.

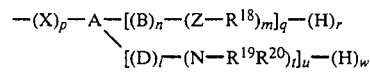

wherein X and Z represent O or S, $R^{18}$, $R^{19}$ and $R^{20}$ represent H or an alkyl group, A, B and D represent a connecting group, n and l is an integer of 0-10, m, q, t, u, r and w are an integer of 0-2, and p is 0 or 1.

15 Claims, 6 Drawing Sheets

FOREIGN PATENT DOCUMENTS

| | | | |
|---|---|---|---|
| 61-140902 | 6/1986 | Japan | 540/140 |
| 1206259 | 9/1986 | Japan | 524/88 |
| 254903 | 11/1986 | Japan | 540/140 |
| 1116904 | 5/1989 | Japan | 430/78 |
| 1233401 | 9/1989 | Japan . | |
| 3031247 | 2/1991 | Japan . | |
| 3203948 | 9/1991 | Japan . | |
| 8700176 | 1/1987 | WIPO . | |
| 88/06175 | 8/1988 | WIPO . | |

OTHER PUBLICATIONS

Matsura et al. Chemical Abstracts vol. 112, 1990 Abstract 66371.

TDK Corp., Chemical Abstracts vol. 107, 1987 Abstract 87329p.

Cooper, Spectroscopic Techniques for Organic Chemists (New York 1980). Wiley and Sons p. 3.

PHTHALOCYANINE COMPOUNDS AND USAGE THEREOF

BACKGROUND OF THE INVENTION

1) Field of the Invention

This invention relates to green dyes, which can play an important role in color filters for display devices such as liquid crystal television sets or in color separation filters for image pickup tubes or color copying machines, and also to color filters. The present invention is also concerned with near infrared absorbers, which can play an important role in optoelectronics-related fields such as recording of information, image sensors and protective goggles, and also with optical recording media fabricated using the near infrared absorbers.

2) Description of the Related Art

Known conventional filters using a phthalocyanine compound include inter alia those disclosed in Japanese Patent Laid-Open Nos. 30509/1984, 249102/1985, 140902/1986, 254903/1986, 254904/1986, 6904/1989, 88505/1989 and 233401/1989.

Among such phthalocyanine compounds, water-soluble compounds containing one or more sulfonic groups are suited for coloring filters in which gelatin or casein is used as a base material, and have been employed in gelatin-base filters. These filters have, however, been used only to a limited extent due to the poor heat resistance and moisture resistance of the filters per se. The phthalocyanine compounds containing substituents at the β-positions thereof, which are disclosed in Japanese Patent Laid-Open No. 233401/1989, are excellent in durability but are not sufficient in transmission characteristics. On the other hand, phthalocyanine compounds containing substituents at the α-positions, which are disclosed in WO 88/06175 and GB 2168372A, are accompanied by the drawback that they have poor solubility in resins and, to obtain a color density useful as a green filter, the film thickness of the filter must be increased. Further, their transmittance characteristics as green dyes are not sufficient.

Usage of phthalocyanine compounds as near infrared absorbers is widely known, for example, from Japanese Patent Laid-Open Nos. 209583/1985, 152769/1986, 154888/1986, 197280/1986, 246091/1986 and 39286/1987. The absorption ability of these phthalocyanine compounds was however not sufficient as they are prone to association. Optical recording media making use of one or more of such phthalocyanine compounds are, therefore, accompanied by drawbacks such as low reflectance at 780–830 nm and insufficient sensitivity and recording characteristics.

SUMMARY OF THE INVENTION

An object of this invention is to improve the poor solubility in a binder resin, transmittance characteristics, light resistance and heat resistance, which are the drawbacks common to such conventional green filters as described above and also to such green filter dyes as referred to above.

Another object of this invention is to provide a novel near infrared absorber free of the above-mentioned drawbacks and also an optical recording medium fabricated using the novel near infrared absorber and having high reflectance and good sensitivity and recording characteristics.

A further object of this invention is to provide a near infrared absorber, which has high solubility in liquid crystal compounds employed in liquid crystal devices and also exhibits good sensitivity to laser beam writing.

The present inventors have conducted extensive research with a view toward attaining the above objects. As a result, it has been found that the solubility in a resin can be improved by the use of a phthalocyanine compound substituted at the α-position thereof by particular substituents, preferably each substituent containing one or more hetero atoms, desirably one or more nitrogen atoms, thereby making it possible to obtain a filter having good transmittance characteristics and excellent durability such as heat resistance and light resistance. As reasons for the good transmittance characteristics of the phthalocyanine compounds with hetero-atom-containing substituents at the α-positions, it may be mentioned that the introduction of the hetero atom in the side chain makes the polarity of the dye similar to that of the resin and, as a result, the compatibility between the resin and the dye is improved and the dye is stably distributed as discrete molecules in the resin.

It has also been found that the phthalocyanine compounds substituted at the α-positions by N-containing substituents exhibit sharp absorption at 650–900 nm, have a high molecular absorption coefficient and are excellent as near infrared absorbers. Optical recording media making use of one or more of these near infrared absorbers have been found to have high reflectance and sensitivity in the near infrared range. As reasons for the good absorbing ability of the phthalocyanine compounds substituted at the α-position by N-containing substituents, it can be mentioned that association of molecules is suppressed owing to the action of nitrogen atoms.

The present invention, therefore, provides a color filter and a near infrared absorber, both comprising a phthalocyanine compound represented by the following formula (I), and an optical recording medium and a liquid crystal display device, both fabricated using the same:

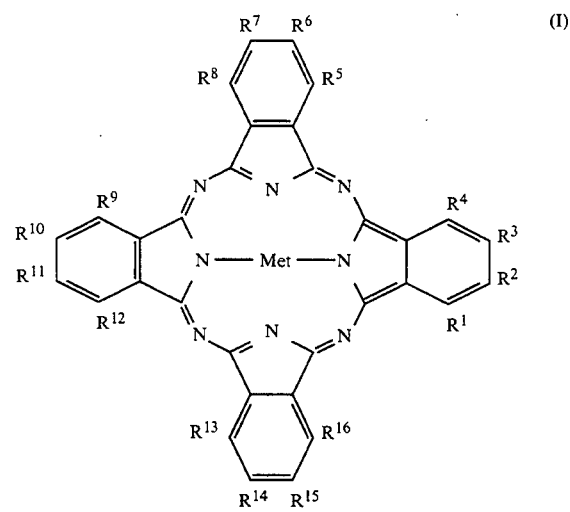

wherein $R^1$, $R^4$, $R^5$, $R^8$, $R^9$, $R^{12}$, $R^{13}$ and $R^{16}$ independently represent a group represented by the below-described formula (II) or a hydrogen or halogen atom with the proviso that, in each of the combinations of $R^1$ and $R^4$, $R^5$ and $R^8$, $R^9$ and $R^{12}$, and $R^{13}$ and $R^{16}$, at least one of the groups is represented by the formula (II); $R^2$, $R^3$, $R^6$, $R^7$, $R^{10}$, $R^{11}$, $R^{14}$ and $R^{15}$ independently represent a substituted or unsubstituted $C_{1-20}$ alkyl, substituted or unsubstituted $C_{1-20}$ alkoxyl group, substituted or unsubstituted $C_{1-20}$ alkylthio, substituted or unsubstituted $C_{1-20}$ alkylamino, substituted or unsubstituted $C_{2-20}$ dialkylamino, substituted or unsubstituted aryloxy, substituted or unsubstituted arylthio, —COOR$^{17}$, $R^{17}$ being a hydrogen atom or a substituted or unsubstituted alkyl group, hydroxyl or mercapto group or a halogen or hydrogen atom; and Met represents a metal atom.

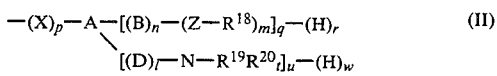

wherein X and Z represent an oxygen or sulfur atom, $R^{18}$, $R^{19}$ and $R^{20}$ independently represent a hydrogen atom or a substituted or unsubstituted $C_{1-20}$ alkyl group, A, B and D represent a connecting group, n and l stand for an integer of 0–10, m, q, t, u, r and w are an integer of 0–2, and p represents 0 or 1.

The present invention also provides a phthalocyanine compound represented by the following formula (III):

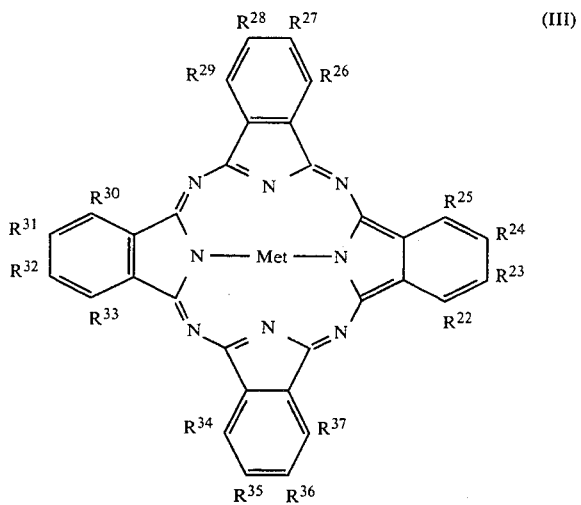

where in $R^{22}$, $R^{25}$, $R^{26}$, $R^{29}$, $R^{30}$, $R^{33}$, $R^{34}$ and $R^{37}$ independently represent a group represented by the below-described formula (IV) or a hydrogen or halogen atom with the proviso that, in each of the combinations of $R^{22}$ and $R^{25}$, $R^{26}$ and $R^{29}$, $R^{30}$ and $R^{33}$, and $R^{34}$ and $R^{37}$, at least one of the groups is represented by the formula (IV); $R^{23}$, $R^{24}$, $R^{27}$, $R^{28}$, $R^{31}$, $R^{32}$, $R^{35}$ and $R^{36}$ independently represent a substituted or unsubstituted $C_{1-20}$ alkyl, substituted or unsubstituted $C_{1-20}$ alkoxyl group, substituted or unsubstituted $C_{1-20}$ alkylthio, substituted or unsubstituted $C_{1-20}$ alkylamino, substituted or unsubstituted $C_{2-20}$ dialkylamino, substituted or unsubstituted aryloxy, substituted or unsubstituted arylthio, —COOR$^{38}$, $R^{38}$ being a hydrogen atom or a substituted or unsubstituted alkyl group, hydroxyl or mercapto group or a halogen or hydrogen atom; and Met represents a metal atom; said formula (IV) being a group of the formula

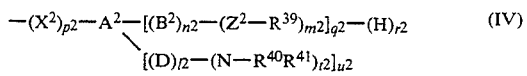

wherein $X^2$ and $Z^2$ represent an oxygen or sulfur atom, $R^{39}$, $R^{40}$ and $R^{41}$ independently represent a hydrogen atom or a substituted or unsubstituted $C_{1-20}$ alkyl group, $A^2$, $B^2$ and $D^2$ represent a connecting group, $n^2$ and $l^2$ stand for an integer of 0–10, $m^2$ represents an integer of 0–3, $r^2$ and $q^2$ represent an integer of 0–2, $u^2$ is an integer of 1–2, $t^2$ is an integer of 1–3, and $p^2$ presents 0 or 1.

BRIEF DESCRIPTION OF THE DRAWINGS

FIG. 1 through FIG. 3 illustrate fabrication steps of a color filter according to the present invention, in which FIG. 1 shows a substrate coated with a photo-sensitive resin containing a phthalocyanine compound of this invention, FIG. 2 illustrates an exposure step to light through a mask pattern, and FIG. 3 depicts a monochromatic color filter from which unexposed areas have been removed by development;

FIGS. 5 through 9 show transmittance spectra of color filters, respectively, in which FIG. 5 depicts a transmittance spectrum of a color filter containing the phthalocyanine compound of Example 1, FIG. 6 a transmittance spectrum of a color filter containing the phthalocyanine compound of Example 2, FIG. 7 a transmittance spectrum of a color filter containing the phthalocyanine compound of Example 3, FIG. 8 a transmittance spectrum of a color filter containing the phthalocyanine compound of Comparative Example 1, and FIG. 9 a transmittance spectrum of a color filter containing the phthalocyanine compound of Comparative Example 2.

DETAILED DESCRIPTION OF THE PREFERRED EMBODIMENTS

Figure 1:
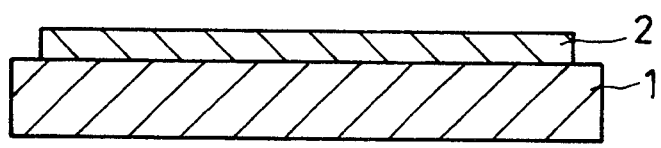

Preferred embodiments of this invention will hereinafter be described.

In the formula (I), examples of the unsubstituted $C_{1-20}$ alkyl group represented by $R^2$, $R^3$, $R^6$, $R^7$, $R^{10}$, $R^{11}$, $R^{14}$ or $R^{15}$ include linear, branched and cyclic alkyl groups such as methyl, ethyl, n-propyl, n-butyl, n-pentyl, n-hexyl, n-dodecyl, cyclopentyl, cyclohexyl, n-heptyl, n-octyl, and n-nonyl.

Exemplary substituted $C_{1-20}$ alkyl groups include alkylalkyl groups such as isopropyl, iso-butyl, sec-butyl, t-butyl, iso-pentyl, neo-pentyl, 1,2-dimethylpropyl, 2-methylbutyl, 2-methylpentyl, 1,3-dimethylbutyl, 1-iso-propylpropyl, 1,2-dimethylbutyl, 1,4-dimethylpentyl, 2-methyl-1-iso-propylpropyl, 1-ethyl-3-methylbutyl, 2-ethylhexyl, 3-methyl-1-iso-propylbutyl and 2,2-dimethyl-1-iso-propyl-1-t-butylpropyl; alkoxyalkyl groups such as methoxymethyl, methoxyethyl, ethoxyethyl, propoxyethyl, butoxyethyl, γ-methoxypropyl, γ-ethoxypropyl, methoxyethoxyethyl, ethoxyethoxyethyl, dimethoxymethyl, diethoxymethyl, dimethoxyethyl, and diethoxyethyl; halogenated alkyl groups such as chloromethyl, 2,2,2-trichloroethyl, trifluoromethyl and 1,1,1,3,3,3-hexafluoro-2-propyl; and hydroxyalkyl groups such as hydroxymethyl, hydroxyethyl, hydroxypropyl, hydroxybutyl, hydroxypentyl and hydroxyoctyl.

Examples of the substituted or unsubstituted $C_{1-20}$ alkoxy group include unsubstituted alkoxyl groups such as methoxy, ethoxy, n-propoxy, iso-propoxy, n-butoxy, iso-butoxy, sec-butoxy, t-butoxy, n-pentoxy, iso-pentoxy, neo-pentoxy, n-hexyloxy, cyclohexyloxy, n-heptyloxy, n-octyloxy, n-nonyloxy and n-decyloxy; alkylalkoxyl groups such as 1,2-dimethylpropoxy, 1,3-dimethylbutoxy, 1-iso-propylpropoxy, 1,2-dimethylbutoxy, 1,4-dimethylpentyloxy, 2-methyl-1-iso-propylpropoxy, 1-ethyl-3-methylbutoxy, 2-ethylhexyloxy, 3-methyl-1-iso-propylbutoxy, 2-methyl-1-iso-propylbutoxy and 1-t-butyl-2-methylpropoxy; alkoxyalkoxyl groups such as methoxymethoxy, methoxyethoxy, ethoxyethoxy, propoxyethoxy, butoxyethoxy, γ-methoxypropoxy, γ-ethoxypropoxy, methoxyethoxyethoxy, ethoxyethoxyethoxy, dimethoxymethoxy, diethoxymethoxy, dimethoxyethoxy, and diethoxyethoxy; halogenated alkoxyl groups such as chloromethoxy, 2,2,2-trichloroethoxy, trifluoromethoxy, and 1,1,1,3,3,3-hexafluoro-2-propoxy; and hydroxyalkoxyl groups such as hydroxymethoxy, hydroxyethoxy, hydroxypropoxy, hydroxybutoxy, hydroxypentyloxy, and hydroxyoctyloxy.

Examples of the unsubstituted $C_{1-20}$ alkylthio group include methylthio, ethylthio, n-propylthio, iso-propylthio, n-butylthio, iso-butylthio, sec-butylthio, t-butylthio, n-pentylthio, iso-pentylthio, neo-pentylthio, 1,2-dimethylpropylthio, n-hexylthio, cyclohexylthio, 1,3-dimethylbutylthio, 1-iso-propylpropylthio, 1,2-dimethylbutylthio, n-heptylthio, 1,4-dimethylpentylthio, 2-methyl-1-iso-propylpropylthio, 1-ethyl-3-methylbutylthio, n-octylthio, 2-ethylhexylthio, 3-methyl-1-iso-propylbutylthio, 2-methyl-1-iso-propylbutylthio, 1-t-butyl-2-methylpropylthio, n-nonylthio and n-decylthio groups. Exemplary substituted alkylthio groups include alkylthioalkylthio groups such as methylthiomethylthio, methylthioethylthio, ethylthioethylthio, propylthioethylthio; halogenated alkylthio groups such as chloromethylthio, 2,2,2-trichloroethylthio, trifluoromethylthio, 1,1,1,3,3,3-hexafluoro-2-propylthio; and mercaptoalkylthio groups such as mercaptomethylthio, mercaptoethylthio, mercaptopropylthio, mercaptobutylthio, mercaptopentylthio, and mercaptooctylthio.

Examples of the unsubstituted $C_{1-20}$ alkylamino groups include methylamino, ethylamino, n-propylamino, iso-propylamino, n-butylamino, iso-butylamino, sec-butylamino, t-butylamino, n-pentylamino, iso-pentylamino, neo-pentylamino, 1,2-dimethylpropylamino, n-hexylamino, n-dodecylamino, 2-methylbutylamino, 2-methylpentylamino, cyclopentylamino, cyclohexylamino, 1,3-dimethylbutylamino, 1-iso-propylpropylamino, 1,2-dimethylbutylamino, n-heptylamino, 1,4-dimethylpentylamino, 2-methyl-1-iso-propylpropylamino, 1-ethyl-3-methylbutylamino, n-octylamino, 2-ethylhexylamino, 3-methyl-1-iso-propylbutylamino, 2,2-dimethyl-1-iso-propyl-1-t-butylpropylamino and n-nonylamino groups. Exemplary substituted alkylamino groups include alkoxyalkylamino groups such as methoxymethylamino, methoxyethylamino, ethoxyethylamino, propoxyethylamino, butoxyethylamino, γ-methoxypropylamino, γ-ethoxypropylamino, methoxyethoxyethylamino, ethoxyethoxyethylamino, dimethoxymethylamino, diethoxymethylamino, dimethoxyethylamino, and diethoxyethylamino; halogenated alkylamino groups such as chloromethylamino, 2,2,2-trichloroethylamino, trifluoromethylamino, 1,1,1,3,3,3-hexafluoro-2-propylamino; and hydroxyalkylamino groups such as hydroxymethylamino, hydroxyethylamino, hydroxypropylamino, hydroxybutylamino, hydroxypentylamino, hydroxyoctylamino.

Illustrative of the unsubstituted $C_{2-20}$ dialkylamino group include dimethylamino, diethylamino, di(n-propyl)amino, di(iso-propyl)amino, di(n-butyl)amino, di(iso-butyl)amino, di(sec-butyl)amino, di(t-butyl)amino, di(n-pentyl)amino, di(iso-pentyl)amino, di(neopentyl)amino, di(1,2-dimethylpropyl)amino, di(n-hexyl)amino, di(n-dodecyl)amino, di(2-methylbutyl)amino, di(2-methylpentyl)amino, di(cyclopentyl)amino, di(cyclohexyl)amino, di(1,3-dimethylbutyl)amino, di(1-iso-propylpropyl)amino, di(1,2-dimethylbutyl)amino, di(n-heptyl)amino, di(1,4-dimethylpentyl)amino, di(2-methyl-1-iso-propylpropyl)amino, di(1-ethyl-3-methylbutyl)amino, di(n-octyl)amino, di(2-ethylhexyl)amino, di(3-methyl-1-iso-propylbutyl)amino, di(2,2,-dimethyl-1-iso-propyl-1-t-butylpropyl)amino and di(n-nonyl)amino groups. Examples of the substituted dialkylamino group include di(alkoxyalkyl)amino groups such as di(methoxymethyl)amino, di(methoxyethyl)amino, di(ethoxyethyl)amino, di(propoxyethyl)amino, di(butoxyethyl)amino, di(γ-methoxypropyl)amino, di(γ-ethoxypropyl)amino, di(methoxyethoxyethyl)amino, di(ethoxyethoxyethyl)amino, bis(dimethoxymethyl)amino, bis(diethoxymethyl)amino, bis(dimethoxyethyl)amino, bis(diethoxyethyl)amino; and di(halogenated alkyl)amino groups such as di(chloromethyl)amino, di(2,2,2-trichloroethyl)amino, di(trifluoromethyl)amino and di(1,1,1,3,3,3-hexafluoro-2-propyl)amino groups; and di(hydroxyalkyl)amino groups such as di(hydroxymethyl)amino, di(hydroxyethyl)amino, di(hydroxypropyl)amino, di(hydroxybutyl)amino, di(hydroxypentyl)amino, and di(hydroxyoctyl)amino.

Illustrative of the substituted or unsubstituted aryloxy group include a phenoxy group, which may be substituted by one or more alkyl groups such as methyl, ethyl, propyl, iso-propyl, butyl, 2-methylpropyl, pentyl and/or neo-pentyl, by one or more alkoxyl groups such as methoxy, ethoxy and/or propoxy, and/or by one or more halogen atoms such as chlorine, fluorine, bromine and/or iodine.

Illustrative of the substituted or unsubstituted arylthio group include a phenylthio group, which may be substituted by one or more alkyl groups such as methyl, ethyl, propyl, iso-propyl, butyl, 2-methylpropyl, pentyl and/or neo-pentyl, by one or more alkoxyl groups such as methoxy, ethoxy and/or propoxy, and/or by one or more halogen atoms such as chlorine, fluorine, bromine and/or iodine.

Examples of the halogen atom include chlorine, bromine, iodine and fluorine atoms.

Examples of the unsubstituted alkyl group represented by $R^{17}$ include linear, branched and cyclic alkyl groups such as methyl, ethyl, n-propyl, iso-propyl, n-butyl, iso-butyl, sec-butyl, t-butyl, n-pentyl, iso-pentyl, neo-pentyl, 1,2-dimethylpropyl, n-hexyl, n-dodecyl, 2-methylbutyl, 2-methylpentyl, cyclopentyl, cyclohexyl, 1,3-dimethylbutyl, 1-iso-propylpropyl, 1,2-dimethylbutyl, n-heptyl, 1,4-dimethylpentyl, 2-methyl-1-iso-propylpropyl, 1-ethyl-3-methylbutyl, n-octyl, 2-ethylhexyl, 3-methyl-1-iso-propylbutyl, 2,2-dimethyl-1-iso-propyl-1-t-butylpropyl, and n-nonyl. Examples of the substituted alkyl group include alkoxyalkyl groups such as methoxymethyl, methoxyethyl, ethoxyethyl, propoxyethyl, butoxyethyl, γ-methoxypropyl, γ-ethoxypropyl, methoxyethoxyethyl, ethoxyethoxyethyl, dimethoxymethyl, diethoxymethyl, dimethoxyethyl, diethoxyethyl; halogenated alkyl groups such as chloromethyl, 2,2,2-trichloroethyl, trifluoromethyl, and 1,1,1,3,3,3-hexafluoro-2-propyl; and hydroxyalkyl groups such as hydroxymethyl, hydroxyethyl, hydroxypropyl, hydroxybutyl, hydroxypentyl, hydroxyoctyl.

Examples of the metal represented by Met include Zn, Mg, Si, Sn, Rh, Pt, Pd, Mo, Mn, Pb, Cu, Ni, Co and Fe and also include metal chlorides such as AlCl, INCl, FeCl, $TiCl_2$, $SnCl_2$, $SiCl_2$ and $GeCl_2$, metal oxides such as TiO and VO, and metal hydroxides such as $Si(OH)_2$.

Illustrative of the substituted or unsubstituted $C_{1-20}$ alkyl group represented by $R^{18}$, $R^{19}$ or $R^{20}$ in Formula (II) include those exemplified above with respect to the alkyl group in Formula (I). The connecting group represented by A can be any trivalent or tetravalent connecting group. Preferred examples of the trivalent connecting group include:

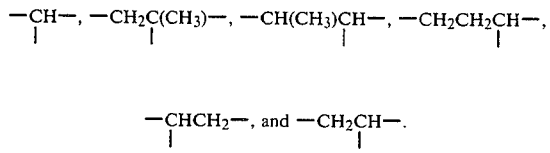

One example of the tetravalent connecting group is

The connecting group represented by B can be any divalent, trivalent or tetravalent connecting group. Preferred examples include —$CH_2$—, —$OCH_2$—, —$OCH_2CH_2$—, —$OCH_2CH_2CH_2$—, —$OCH_2CH(CH_3)$—, —$OCH(CH_3)CH_2$—, —$SCH_2$—, —$SCH_2CH_2$—, —$SCH_2CH_2CH_2$—, —$SCH_2CH(CH_3)$— and —$SCH(CH_3)CH_2$—. The connecting group represented by D can be any divalent, trivalent or tetravalent connecting group. Preferred examples include —$CH_2$—, —$OCH_2$—, —$OCH_2CH_2$—, —$OCH_2CH_2CH_2$—, —$OCH_2CH(CH_3)$—, —$OCH(CH_3)CH_2$—, —$SCH_2$—, —$SCH_2CH_2$—, —$SCH_2CH_2CH_2$—, —$SCH_2CH(CH_3)$—, —$SCH(CH_3)CH_2$—, —$CH(CH_3)$—, —$CH(CH_3)CH_2$—, —$CH(CH_2CH_3)$— and —$CH(CH_2CH_2CH_3)$—, with —$CH_2$—, —$OCH_2$—, —$OCH_2CH_2$—, —$OCH_2CH_2CH_2$—, —$OCH_2CH(CH_3)$— and —$OCH(CH_3)CH_2$— being more preferred.

Specific phthalocyanine compounds include Compound Nos. I-1 to I-124 shown in Table 1. The phthalocyanine compounds may be mixtures of their available isomers. Especially, the phthalocyanine compounds ranging from Compound No. I-1 to Compound No. I-78 and from Compound No. I-121 to Compound No. 124 are suited for use in color filters, near infrared absorbers and optical recording media while the phthalocyanine compounds ranging from Compound No. I-79 to Compound No. I-120 are suited for use in color filters.

TABLE 1

| Compound | R¹, R⁵, R⁹, R¹³ | R², R⁶, R¹⁰, R¹⁴ | R³, R⁷, R¹¹, R¹⁵ | R⁴, R⁸, R¹², R¹⁶ | Met |
|---|---|---|---|---|---|
| I-1 | (structure) | H | H | H | Cu |
| I-2 | (structure) | H | H | H | Cu |
| I-3 | (structure) | H | H | H | Cu |
| I-4 | (structure) | H | H | H | VO |
| I-5 | (structure) | H | H | H | Cu |
| I-6 | (structure) | Br | H | Cl | Fe |
| I-7 | (structure) | H | H | Br | Cu |
| I-8 | (structure) | H | H | H | Fe |
| I-9 | (structure) | PhS | PhS | H | Cu |

TABLE 1-continued

| Compound | R¹, R⁵, R⁹, R¹³ | R², R⁶, R¹⁰, R¹⁴ | R³, R⁷, R¹¹, R¹⁵ | R⁴, R⁸, R¹², R¹⁶ | Met |
|---|---|---|---|---|---|
| I-10 | (structure) | H | H | H | Cu |
| I-11 | (structure) | H | H | H | Co |
| I-12 | (structure) | H | H | H | Cu |
| I-13 | (structure) | H | H | H | Cu |
| I-14 | (structure) | H | H | H | Zn |
| I-15 | (structure) | Cl | Cl | (structure) | Cu |
| I-16 | (structure) | H | H | (structure) | Fe |

TABLE 1-continued

| Compound | R¹, R⁵, R⁹, R¹³ | R², R⁶, R¹⁰, R¹⁴ | R³, R⁷, R¹¹, R¹⁵ | R⁴, R⁸, R¹², R¹⁶ | Met |
|---|---|---|---|---|---|
| I-17 | [structure] | Cl | H | [structure] | Fe |
| I-18 | [structure] | I | I | H | VO |
| I-19 | [structure] | I | H | Br | VO |
| I-20 | [structure] | Br | Br | H | Cu |
| I-21 | [structure] | Br | Br | Br | Co |
| I-22 | [structure] | H | H | H | InCl |
| I-23 | [structure] | S—CH₃ | S—CH₃ | H | Cu |
| I-24 | [structure] | SPh | SPh | H | Cu |

TABLE 1-continued

| Compound | R¹, R⁵, R⁹, R¹³ | R², R⁶, R¹⁰, R¹⁴ | R³, R⁷, R¹¹, R¹⁵ | R⁴, R⁸, R¹², R¹⁶ | Met |
|---|---|---|---|---|---|
| I-25 | —N(CH₃)CH₂CH₂OCH₂CH₂OCH₃ | H | H | H | Mn |
| I-26 | —N(CH₂CH=CH₂)CH₂CH₂OCH₂CH₂OCH₃ | Br | Br | H | Co |
| I-27 | —OCH₂CH(CH₃)CH(OCH₃)CH₂N(CH₃)₂ | Cl | Cl | Cl | Fe |
| I-28 | —N(CH₂CH=CH₂)CH₂CH₂OCH₂CH₂OCH₃ | H | H | Cl | Zn |
| I-29 | —N(CH=CH₂)CH₂CH₂OCH₃ | —S-C₆H₄-Cl | —S-C₆H₄-Cl | —N(CH=CH₂)CH₂CH₂OCH₃ | Cu |
| I-30 | —N(CH₂CH=CH₂)CH₂CH₂OCH₂CH₂OCH₃ | H | H | —N(CH₂CH=CH₂)CH₂CH₂OCH₂CH₂OCH₃ | Zn |
| I-31 | —N(CH₂CH=CH₂)CH₂CH₂OCH₂CH₂OCH₃ | H | Br | H | Cu |
| I-32 | —N(CH₂CH=CH(CH₃))CH₂CH₂OCH₂CH₂OCH₃ | H | H | Br | Cu |
| I-33 | —N(CH₂CH=CH₂)CH₂CH₂OCH₂CH₂OCH₂CH₂OCH₃ | H | I | H | Pd |

TABLE 1-continued

| Compound | R¹, R⁵, R⁹, R¹³ | R², R⁶, R¹⁰, R¹⁴ | R³, R⁷, R¹¹, R¹⁵ | R⁴, R⁸, R¹², R¹⁶ | Met |
|---|---|---|---|---|---|
| I-34 | (allyl-N-CH₂-CH(OCH₃)-CH₂-O-) group | H | H | (allyl-N-CH₂-CH(OCH₃)-CH₂-O-) group | SiC₂ |
| I-35 | (allyl-N-CH₂-CH(OCH₃)-CH₂-O-) group | SPh | SPh | (allyl-N-CH₂-CH(OCH₃)-CH₂-O-) group | Pb |
| I-36 | (allyl-N-CH₂-CH₂-O-) group | H | H | H | Cu |
| I-37 | (allyl-N-CH₂-CH₂-O-) group | Br | Br | Br | Cu |
| I-38 | (allyl-N-CH₂-CH₂-O-) group | H | H | (allyl-N-CH₂-CH₂-O-) group | VO |
| I-39 | (allyl-N-CH₂-CH₂-) group | Cl | H | H | Fe |
| I-40 | (allyl-N-CH₂-CH₂-) group | H | H | (allyl-N-CH₂-CH₂-) group | Cu |
| I-41 | (allyl-N-CH₂-CH(SMe)-CH₂-S-) group | H | H | H | Cu |
| I-42 | (allyl-N-CH₂-CH(S-)-CH₂-S-) group | H | H | H | Cu |
| I-43 | (allyl-N-CH₂-CH(S-)-CH₂-S-) group | H | H | H | Cu |

TABLE 1-continued

| Compound | R¹, R⁵, R⁹, R¹³ | R², R⁶, R¹⁰, R¹⁴ | R³, R⁷, R¹¹, R¹⁵ | R⁴, R⁸, R¹², R¹⁶ | Met |
|---|---|---|---|---|---|
| I-44 | (structure) | H | H | H | Co |
| I-45 | (structure) | H | H | H | Cu |
| I-46 | (structure) | H | H | H | Fe |
| I-47 | (structure) | H | H | H | Fe |
| I-48 | (structure) | H | H | H | Cu |
| I-49 | (structure) | H | H | H | VO |
| I-50 | (structure) | H | H | H | InCl |

TABLE 1-continued

| Compound | R¹, R⁵, R⁹, R¹³ | R², R⁶, R¹⁰, R¹⁴ | R³, R⁷, R¹¹, R¹⁵ | R⁴, R⁸, R¹², R¹⁶ | Met |
|---|---|---|---|---|---|
| I-51 | (structure with SCH₃) | H | H | H | SiCl₂ |
| I-52 | (structure with SCH₃) | H | H | H | Zn |
| I-53 | (structure) | H | H | Br | InCl |
| I-54 | (structure) | I | H | I | Mn |
| I-55 | (structure) | Cl | Cl | (structure) | Cu |
| I-56 | (structure) | H | H | Cl | Cu |
| I-57 | (structure) | H | H | H | Cu |

TABLE 1-continued
| Compound | R¹, R⁵, R⁹, R¹³ | R², R⁶, R¹⁰, R¹⁴ | R³, R⁷, R¹¹, R¹⁵ | R⁴, R⁸, R¹², R¹⁶ | Met |
|---|---|---|---|---|---|
| I-58 | 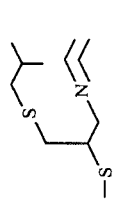 | SPh | SPh | H | Cu |
| I-59 | 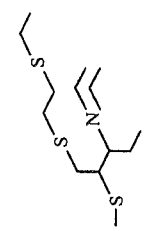 | SPh | SPh | Cl | Pd |
| I-60 | 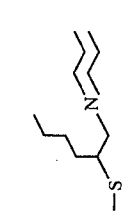 | H | Br | Br | Co |
| I-61 | 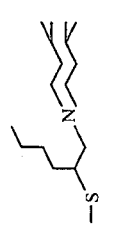 | S—CH₃ | S—CH₃ | H | Zn |
| I-62 | 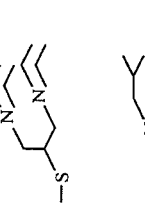 | H | CH₃ | Br | Fe |
| I-63 | 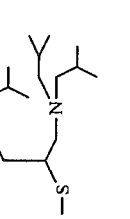 | H | C₂H₅ | H | Fe |
| I-64 | 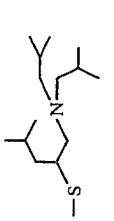 | NHC₂H₅ | NHC₂H₅ | H | VO |

TABLE 1-continued

| Compound | R¹, R⁵, R⁹, R¹³ | R², R⁶, R¹⁰, R¹⁴ | R³, R⁷, R¹¹, R¹⁵ | R⁴, R⁸, R¹², R¹⁶ | Met |
|---|---|---|---|---|---|
| I-65 | [structure] | OPh | OPh | H | SiCl₂ |
| I-66 | [structure] | [4-Cl-phenoxy structure] | [4-Cl-phenoxy structure] | Cl | Si(OH)₂ |
| I-67 | [structure] | H | H | H | Cu |
| I-68 | [structure] | H | H | Cl | VO |
| I-69 | [structure] | [4-Cl-thiophenyl structure] | [4-Cl-thiophenyl structure] | H | Cu |
| I-70 | [structure] | COO—CH₃ | H | H | Cu |
| I-71 | [structure] | N(CH₃)₂ | N(CH₃)₂ | H | Co |
| I-72 | [structure] | SH | SH | H | Co |

TABLE 1-continued

| Compound | R¹, R⁵, R⁹, R¹³ | R², R⁶, R¹⁰, R¹⁴ | R³, R⁷, R¹¹, R¹⁵ | R⁴, R⁸, R¹², R¹⁶ | Met |
|---|---|---|---|---|---|
| I-73 | —S-propyl-S-propyl-N=allyl | H | I | I | Mn |
| I-74 | —S-CH(iPr)-CH₂-N(iPr)-CH₂-CH(CH₃)-S— | 3-chlorophenoxy | 3-chlorophenoxy | H | Fe |
| I-75 | —S-CH(propyl)-CH₂-N(propyl)-CH₂-CH(CH₃)-S— | H | H | —S-CH₂-CH(propyl)-N(propyl)-propyl | Cu |
| I-76 | —S-CH₂-CH₂-N=allyl | Cl | H | Cl | Cu |
| I-77 | —S-CH₂-CH₂-N=CH-CH=CH₂ | Cl | H | —S-CH₂-CH₂-N=CH-CH=CH₂ | Cu |
| I-78 | —S-CH₂-CH₂-N=CH-CH=CH₂ | I | H | —S-CH₂-CH₂-N=CH-CH=CH₂ | Fe |
| I-79 | —CH₂-CH₂-O-CH₂-CH₂-O-CH₂-CH₂-O-CH₃ | H | H | H | Zn |
| I-80 | —CH₂-CH₂-O-CH₂-CH₂-O-CH₃ | H | H | Br | VO |
| I-81 | —CH₂-CH(CH₃)-O-CH₂-CH₂-O-CH₃ | H | H | Cl | VO |
| I-82 | —CH₂-C(CH₃)₂-O-CH₂-CH₂-O-CH₃ | H | H | CH₃ | VO |

TABLE 1-continued
| Compound | R¹, R⁵, R⁹, R¹³ | R², R⁶, R¹⁰, R¹⁴ | R³, R⁷, R¹¹, R¹⁵ | R⁴, R⁸, R¹², R¹⁶ | Met |
|---|---|---|---|---|---|
| I-83 |  | H | Cl |  | Pd |
| I-84 |  | H | I |  | Fe |
| I-85 |  | SPh | SPh | H | Cu |
| I-86 | 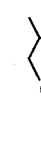 | H | H |  | Cu |
| I-87 |  | Cl | Cl | Cl | Cu |
| I-88 | 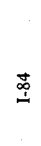 | H | H |  | Fe |
| I-89 | | | | | Fe |
| I-90 | | | | | Co |
| I-91 | | | Cl | Cl | Pd |
| I-92 | | H | I | I | Ni |

TABLE 1-continued

| Compound | R¹, R⁵, R⁹, R¹³ | R², R⁶, R¹⁰, R¹⁴ | R³, R⁷, R¹¹, R¹⁵ | R⁴, R⁸, R¹², R¹⁶ | Met |
|---|---|---|---|---|---|
| I-93 | —O—CH₂CH₂—OH | NH(CH₃) | NH(CH₃) | —O—CH₂CH₂—OH | GeCl₂ |
| I-94 | —O—CH₂—CH(CH₃)—CH₂—OH | H | Cl | —O—CH₂—CH(CH₂OH)— | Zn |
| I-95 | —O—CH(CH₂CH₂OH)— | N(CH₃)₂ | N(CH₃)₂ | H | Zn |
| I-96 | —S—CH₂CH₂—S—CH₂CH₂—S— | —S—C₆H₄—Cl | —S—C₆H₄—Cl | H | Pb |
| I-97 | —S—CH₂CH₂—S—C₂H₅ | H | H | H | Zn |
| I-98 | —S—CH₂CH₂—S—iC₃H₇ | H | H | Br | Cu |
| I-99 | —S—CH₂CH₂—S—iC₄H₉ | H | H | H | Ni |
| I-100 | —S—CH₂CH₂—S—CH₂CH₂—S—iC₄H₉ | H | H | H | Ni |
| I-101 | —S—CH₂CH₂—S—CH₂CH₂—S—CH₂—iC₃H₇ | Cl | Cl | —S—CH₂—CH(S—iC₃H₇)— | Fe |
| I-102 | —S—CH(CH₂—S—iC₄H₉)—CH₂—S—iC₄H₉ | COOC₂H₅ | H | H | Cu |

TABLE 1-continued

| Compound | R¹, R⁵, R⁹, R¹³ | R², R⁶, R¹⁰, R¹⁴ | R³, R⁷, R¹¹, R¹⁵ | R⁴, R⁸, R¹², R¹⁶ | Met |
|---|---|---|---|---|---|
| I-103 | butyl-S-CH(CH₂-S-)CH₂-S- | OH | H | Cl | Zn |
| I-104 | perfluoro-isobutyl-CH₂-S- | H | H | H | Pd |
| I-105 | isobutyl-S- | H | Cl | Cl | Pd |
| I-106 | isopentyl-S- | H | H | sec-butyl-S- | Zn |
| I-107 | sec-butyl-S- | H | H | H | SiCl₂ |
| I-108 | isohexyl-S- | H | Br | H | Fe |
| I-109 | isobutyl-S- | H | H | Br | Co |
| I-110 | HS-CH₂CH₂-S- | H | H | H | Cu |
| I-111 | CH₃CH(SH)CH₂-S- | H | H | HSCH(CH₃)CH₂-S- | Pd |
| I-112 | HSCH₂CH(CH₃)CH₂-S- | H | Cl | Cl | Pb |
| I-113 | hexyl- | H | H | H | Cu |
| I-114 | isobutyl- | H | H | isobutyl- | Cu |
| I-115 | Cl-butyl- | H | Br | Br | Fe |

TABLE 1-continued

| Compound | $R^1, R^5, R^9, R^{13}$ | $R^2, R^6, R^{10}, R^{14}$ | $R^3, R^7, R^{11}, R^{15}$ | $R^4, R^8, R^{12}, R^{16}$ | Met |
|---|---|---|---|---|---|
| I-116 | ~~~Br | H | H | Br | Fe |
| I-117 | ~~~~~~~~ (nonyl) | H | H | H | Fe |
| I-118 | ~~~~~OH | H | H | Br | Cu |
| I-119 | perfluoroalkyl (F F F F / F F F F F) | H | H | H | Cu |
| I-120 | ~~~~~SH | H | H | Cl | Co |
| I-121 | CH₂OCH₂CH(OCH₃)CH₂N(CH₃)CH=CH₂ | OCH₃ | H | H | Cu |
| I-122 | CH₂OCH₂CH(OCH₃)CH₂N(CH₃)CH=CH₂ | OCH₃ | OCH₃ | H | Co |
| I-123 | CH₂OCH₂CH(OCH₃)CH₂N(CH₃)CH=CH₂ | OCH₃ | H | H | Cu |
| I-124 | CH₂OCH₂CH(OCH₂OCH₃)CH₂N(CH₃)CH₂CH₂OCH₃ | H | OC₂H₅ | H | Pb |

The dyes represented by the formula (I) can each be synthesized, for example, by reacting under heat a compound or a mixture of 2-4 compounds, all represented by the following formula (V) or (VI):

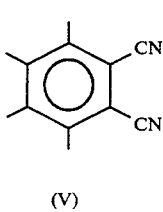  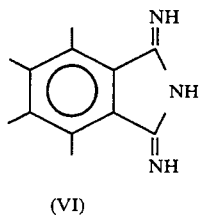

(V)    (VI)

wherein the benzene rings in the formulae (V) and (VI) may optionally have one or more substituents such as those described above in connection with the formula (I), with a metal compound, which is represented by the following formula (VII):

Met-(Y)$_d$  (VII)

wherein Met is the same as Met in formula (I), Y means a monovalent or divalent ligand such as a halogen atom, an anionic acetate ion, acetylacetonato or oxygen atom, and d stands for an integer of 1-4, for example, in the presence of 1,8-diazabicyclo[5.4.0]-7-undecene (DBU), in a solvent such as an alcohol, an alkylaminourea, a halogenated hydrocarbon or quinoline, at 80°-230° C., for about 2-20 hours.

To fabricate a color filter for LCD or a color separation filter for image pickup tube by using one of the phthalocyanine compound of this invention, various processes can be used. For example, a photosensitive resin or photopolymerizable monomer is formed into a film on a substrate by casting, spin coating or the like. After the film being patterned by exposure to light, the resin layer is colored with the dye by dipping or the like. The filter is patterned by dry etching or lifting-off and then colored with the dye by vaccum deposition. The dye is either dissolved or dispersed beforehand in a photosensitive resin or photopolymerizable monomer. The solution or dispersion so prepared is formed into a film on a substrate by casting, spin coating or the like. The film is then patterned by exposure to light. As a still further alternative, such a solution or dispersion is applied in the form of a pattern by a printing method.

As has been described above, the patterning of a dye layer can be conducted on an optically transparent substrate. No particular limitation is imposed on the substrate to be used, insofar as it permits patterning of the dye layer and the color filter so formed functions as desired.

Examples of the substrate include glass plates; and films or plates of resins such as polyvinyl alcohol, hydroxyethylcellulose, methyl methacrylate, polyesters, polybutyral, polyamides, polyethylene, polyvinyl chloride, polyvinylidene chloride, polycarbonates, polyolefin copolymers, vinyl chloride copolymers, vinylidene chloride copolymers and styrene copolymers. A patterned dye layer can also be formed integrally with a substrate which is applied as a color filter. Examples of such a substrate includes the display screen of a cathode ray tube, the image receiving screen of an image pickup tube, a wafer with a solidstate image pickup device such as CCD, BBD, CID or BASIS formed thereon, a contact-type image sensor using a thin-film semiconductor, a liquid crystal display screen, and a photosensitive body or substrate for color electrophotography.

Taking the formation of a stripe filter as an example, a typical process for the formation of a filter will hereinafter be described with reference to the drawings.

First, one of the phthalocyanine compounds according to this invention is dissolved or dispersed at a proportion of 1-100 wt. %, preferably 40-100 wt. % in a photosensitive resin, and the resulting solution or dispersion is spin-coated on a substrate 1 by using a spinner (FIG. 1). The thickness of a resist layer 2 is usually 0.5-100 μm although it is determined depending on spectroscopic characteristics desired. After the resist layer 2 is dried, the resist layer 2 is prebaked under suitable temperature conditions. The resist layer is exposed to light or an electron beam, to which the resist has sensitivity, via a mask 3 having a desired pattern corresponding to a pattern to be formed (i.e., a stripe pattern)—FIG. 2. The resist layer so exposed is then developed to form a pattern 4 (FIG. 3). If necessary, pre-treatment may be applied before the development to release any strain of the resist layer, or rinsing treatment may be conducted after the development to suppress any expansion of the resultant film. Finally, postbaking is applied under appropriate temperature conditions.

Figure 2:
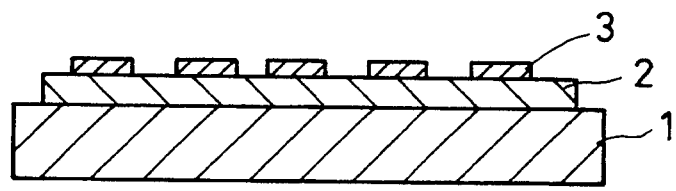
Figure 3:
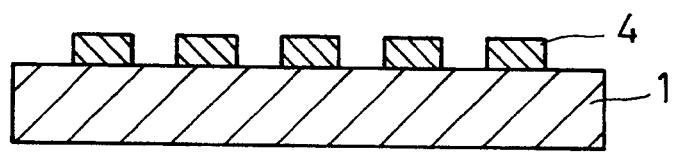
Figure 4:
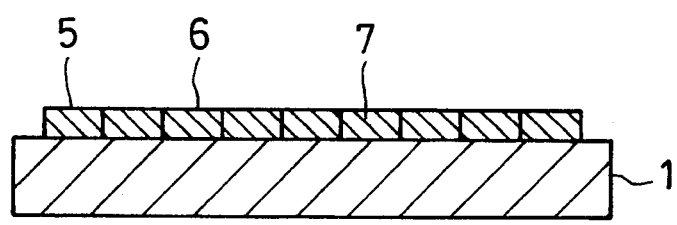
FIG. 4 is a cross-section of a trichromatic color filter.

To form a color filter having two or more colors, the steps of from FIG. 1 to FIG. 3 are repeated using dyes corresponding to the respective colors as needed, namely, as many times as the number of filter colors employed, thereby making it possible to form, for example, a color filter having three colored layers 5,6,7 of different colors as shown in FIG. 4. To form a black matrix, the formation of colored layers may preferably be conducted after the formation of the black matrix.

To fabricate a color filter for a color copying machine or the like by using one of the phthalocyanine compound of this invention, various processes can be used. For example, it can be fabricated by mixing a thermoplastic resin, such as polystyrene, polymethyl methacrylate, polycarbonate, polyester or polyvinyl chloride, with 0.5-10 wt. %, based on the resin, of the dye of this invention and then injection-molding or drawing the resultant resin composition. It can also be fabricated by dissolving the dye of this invention either singly or together with a binder in a solvent and forming the resultant solution into a film on a substrate in accordance with casting, spin coating or the like. As a further alternative, the dye of this invention can be formed into a film on a substrate by vacuum evaporation. As a still further alternative, the dye of this invention is mixed with a varnish which contains a resin intermediate, and the resulting mixture is processed and then heat-treated into a resin.

As the material for the substrate in the above process, any resin can be used as long as it is optically transparent. Illustrative usable resins include acrylic resins, polyethylene, vinyl chloride resin, vinylidene chloride resin, polycarbonates, polyethylene copolymers, polyolefin copolymers, vinyl chloride copolymers, vinylidene chloride copolymers, and styrene copolymers.

To fabricate an optical recording medium by using one of the dyes according to the present invention, the dye can be coated or vacuum-evaporated on a transparent substrate. According to the coating process, a binder resin and the phthalocyanine compound are dissolved in a solvent such that the concentration of the binder resin is not higher than 20 wt. %, preferably 0 wt. % and that of the phthalocyanine compound is 0.05–20 wt. %, preferably 0.5–20 wt. %, and the resultant solution is coated by a spin coater. According to the vacuum evaporation process, the phthalocyanine compound is deposited on the substrate at $10^{-5}$–$10^{-7}$ torr and 100°–300° C.

To allow the phthalocyanine compound of this invention to exhibit good performance different from conventional dyes, spin-coating or dipping should be used. In particular, it is the best process to coat only the phthalocyanine compound of this invention. On the other hand, the optical recording medium can be either of the WORM type that only a recording layer comprising the phthalocyanine compound of this invention is provided on a substrate or of the CD-WORM type that the above recording layer is provided on a substrate, a reflective layer made of gold or aluminum is provided over the recording layer and an over-coat is applied further.

Any resin can be used for the production of the substrate as long as it is optically transparent. Illustrative usable resins include acrylic resins, polyethylene, vinyl chloride resin, vinylidene chloride resin, polycarbonate resins, polyethylene copolymers, polyolefin copolymers, vinyl chloride copolymers, vinylidene copolymers and styrene copolymers.

The substrate may have been surface-treated with a thermosetting resin or an ultraviolet curing resin.

To fabricate an optical recording medium (optical disc, optical card or the like), it is preferable from the standpoints of manufacturing cost and the handling ease by users to employ a polyacrylate substrate or polycarbonate substrate as a substrate and to coat and form a recording layer by spin coating.

In view of the solvent resistance of the substrate, illustrative solvents usable upon spin coating include halogenated hydrocarbons such as dichloromethane, chloroform, carbon tetrachloride, tetrachloroethylene and dichlorodifluoroethane; ethers such as tetrahydrofuran and diethyl ether; ketones such as acetone and methyl ethyl ketone; alcohols such as methanol, ethanol and propanol; cellosolves such as methylcellosolve and ethylcellosolve; and hydrocarbons such as hexane, cyclohexane, octane, benzene, toluene and xylene.

The present invention will hereinafter be described in detail by the following examples. It should be borne in mind that embodiments of this invention should not be limited to or by the following examples.

EXAMPLE 1

In a vessel equipped with a stirrer, a reflux condenser and a nitrogen inlet tube, 10 g of 3-nitrophthalonitrile, 70 g of dried dimethylformamide (DMF) and 30 g of dried toluene were charged. They were thereafter converted completely into a solution, followed by cooling to 0° C. To the resulting solution, 100 g of a solution of 9.8 g of sodium oxide (the compound represented by the below-described formula VII-1), which had been prepared from sodium hydride, in DMF/toluene (7/3) was added dropwise at 0° to −5° C. After the temperature was raised to room temperature, the resulting solution was stirred for 2 hours. The target compound was obtained from the thus-obtained reaction mixture by extracting it with toluene and then purified by column chromatography, whereby 15 g of phthalonitrile (the compound represented by the below-described formula V-1) were obtained.

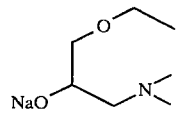
(VII-1)

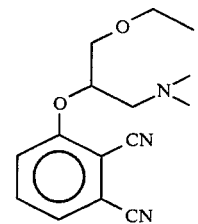
(V-1)

In a vessel equipped with a stirrer, a reflux condenser and a nitrogen inlet tube, 10 g (36.6 mmol) of the above-obtained phthalonitrile (V-1), 5.6 g of 1,8-diazabicyclo[5.4.0]-7-undecene and 100 g of n-amyl alcohol were charged, followed by heating to 110° C. in a nitrogen atmosphere. At the same temperature, 1.2 g (12 mmol) of CuCl were added, followed by reaction at 110°–120° C. for 8 hours. After the completion of the reaction, the reaction mixture was cooled and insoluble matter was removed by filtration. The filtrate was concentrated under reduced pressure to distill off the solvent. The residue was purified by column chromatography, whereby 8.2 g of a mixture consisting of the target compound (I-1) and its isomer(s) were obtained. Physical properties and elemental analysis data of the compound so obtained are shown below:

Visible absorption:
$\lambda_{max} = 698$ nm
$\epsilon g = 2.5 \times 10^5$ ml/g·cm
(Solvent: toluene)

| Elemental analysis: $C_{60}H_{76}N_{12}O_8Cu$ | | | |
| --- | --- | --- | --- |
| | C | H | N |
| Calculated (%) | 62.31 | 6.58 | 14.54 |
| Found (%) | 62.30 | 6.60 | 14.52 |

In 10 g of a prepolymer ("SD-17", trade name; product of Dainippon Ink & Chemicals, Inc.), 5 g of the above-obtained phthalocyanine compound (I-1) and 5 g of "M/P yellow 3GSL" (trade name; product of Mitsui Toatsu Dyes, Ltd.) were dissolved. A glass substrate was spin-coated with the resultant coating formulation by using a spinner. The substrate was prebaked at 85°–100° C. for 2–5 minutes and then exposed (20–30 mj/cm², 2 min.) to light from a high-pressure mercury lamp via a mask having a striped pattern. The resulting substrate was developed so that a pattern was formed thereon. Finally, the substrate was post-baked at 200°–230° C. for 10–30 minutes, whereby a filter with green stripes was obtained. The thickness of the dye layer was 2 μm.

Figure 5:
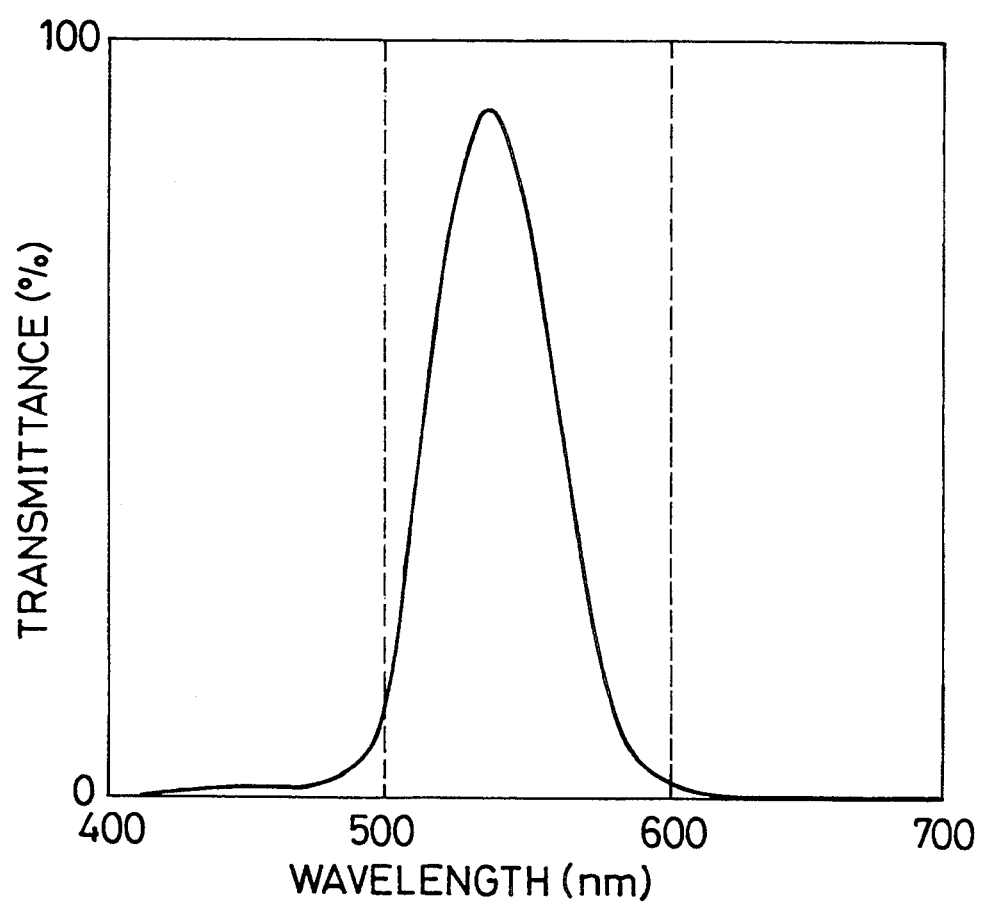

The filter so obtained was superior in durability (moisture resistance, light resistance and heat resistance) and also in transmittance characteristics. The transmittance characteristics are shown in FIG. 5.

In addition, a solution (10 g/l) of the phthalocyanine compound (I-1) in n-octane was coated on a polycarbonate substrate, whereby an optical recording medium with gold as a reflective layer was fabricated. That optical recording medium showed 70% reflectance at 780–830 nm, and also 60 dB sensitivity as measured on the basis of reflection of a 780 nm laser beam of 7 mW from its substrate at 1800 rpm.

EXAMPLE 2

In a vessel equipped with a stirrer, a reflux condenser and a nitrogen inlet tube, 10 g of 3-nitrophthalonitrile, 70 g of dried dimethylformamide (DMF) and 30 g of dried toluene were charged. They were thereafter converted completely into a solution, followed by cooling to 0° C. To the resulting solution, 100 g of a solution of 11.4 g of sodium oxide (the compound represented by the below-described formula VII-2), which had been prepared from sodium hydride, in DMF/toluene (7/3) was added dropwise at 0° to −5° C. After the temperature was raised to room temperature, the resulting solution was stirred for 2 hours. The target compound was obtained from the thus-obtained reaction mixture by extracting it with toluene and then purified by column chromatography, whereby 16 g of phthalonitrile (the compound represented by the below-described formula V-2) were obtained.

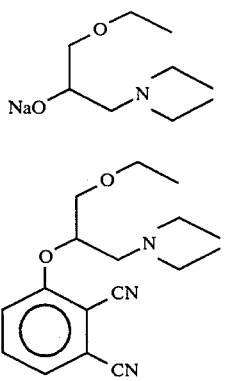

In a vessel equipped with a stirrer, a reflux condenser and a nitrogen inlet tube, 15 g (49.8 mmol) of the above-obtained phthalonitrile (V-2), 7.6 g of 1,8-diazabicyclo[5.4.0]-7-undecene and 100 g of n-amyl alcohol were charged, followed by heating to 110° C. in a nitrogen atmosphere. At the same temperature, 1.48 g (14.9 mmol) of CuCl were added, followed by reaction at 110°–120° C. for 8 hours. After the completion of the reaction, the reaction mixture was cooled and insoluble matter was removed by filtration. The filtrate was concentrated under reduced pressure to distill off the solvent. The residue was purified by column chromatography, whereby 12 g of a mixture consisting of the target compound (I-2) and its isomer(s) were obtained. Physical properties and elemental analysis data of the compound so obtained are shown below:

Visible absorption:
$\lambda_{max} = 698$ nm
$\epsilon g = 2.4 \times 10^5$ ml/g·cm
(Solvent: toluene)

| Elemental analysis: $C_{68}H_{92}N_{12}O_8Cu$ | | | |
|---|---|---|---|
| | C | H | N |
| Calculated (%) | 64.38 | 7.26 | 13.25 |
| Found (%) | 64.35 | 7.32 | 13.27 |

Figure 6:
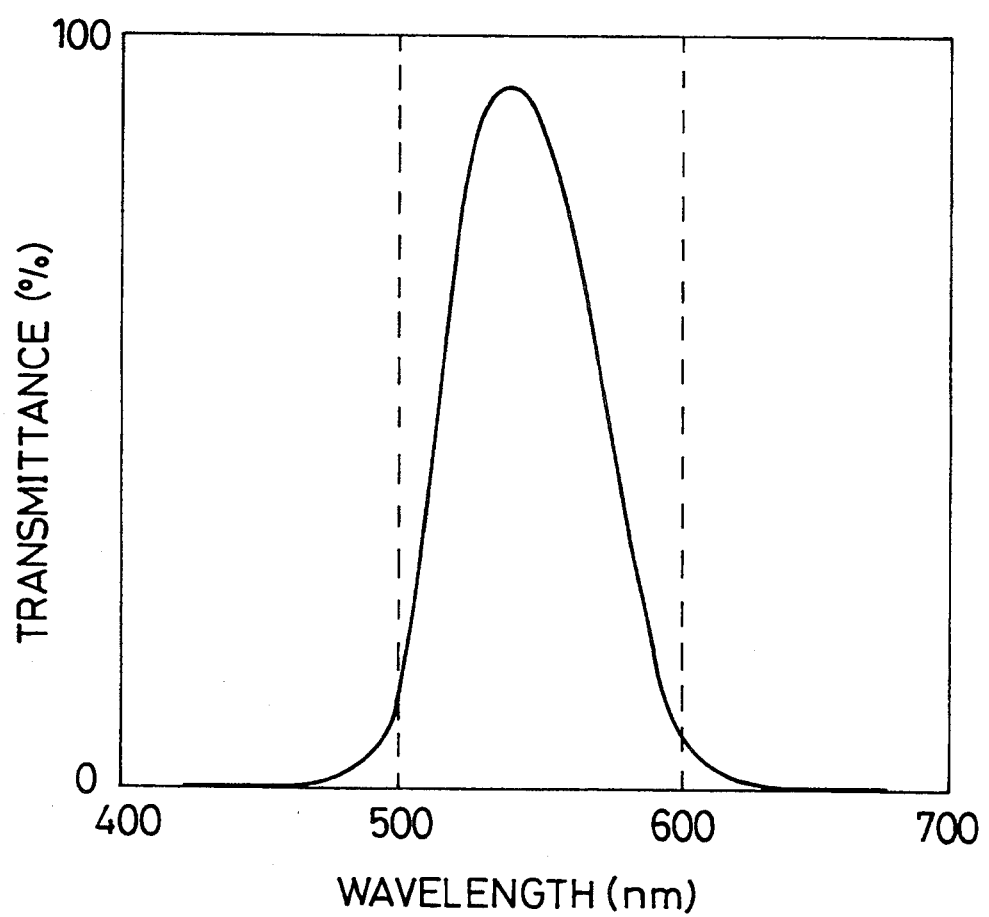

In a vessel equipped with a stirrer and a nitrogen inlet tube, 36.8 g of 4,4'-bis(2-aminophenoxy)biphenyl and 202 g of N,N-dimethylformamide were charged. 4,4'-(p-Phenylenedioxy)diphthalic dianhydride (39.8 g) were added in portions at room temperature in a nitrogen atmosphere, followed by stirring for 20 hours. To the resultant polyamidic acid solution, 3.0 g of the compound (I-2) and 3 g of "M/P yellow 3GSL" were added and mixed. The mixture was thereafter cast on a glass substrate, followed by heat treatment at 200° C. for 5 hours. The filter so obtained was found to have not only good transmittance characteristics but also excellent durability. Its transmittance characteristics are shown in FIG.6.

In addition, a solution of the phthalocyanine compound (I-2) in n-octane (10 g/l) was coated on a polycarbonate substrate, whereby an optical recording medium with gold as a reflective layer was fabricated. That optical recording medium showed 72% reflectance at 780–830 nm, and also 61 dB sensitivity as measured on the basis of reflection of a 780 nm laser beam of 7 mW from its substrate at 1800 rpm.

EXAMPLE 3

In a vessel equipped with a stirrer, a reflux condenser and a nitrogen inlet tube, 10 g of 3-nitrophthalonitrile, 70 g of dried dimethylformamide (DMF) and 30 g of dried toluene were charged. They were thereafter converted completely into a solution, followed by cooling to 0° C. To the resulting solution, 100 g of a solution of 13.8 g of sodium oxide (the compound represented by the below-described formula VII-3), which had been prepared from sodium hydride, in DMF/toluene (7/3) was added dropwise at 0° to −5° C. After the temperature was raised to room temperature, the resulting solution was stirred for 2 hours. The target compound was obtained from the thus-obtained reaction mixture by extracting it with toluene and then purified by column chromatography, whereby 16 g of phthalonitrile (the compound represented by the below-described formula V-3) were obtained.

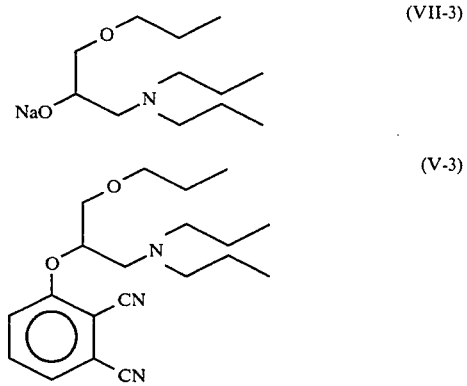

In a vessel equipped with a stirrer, a reflux condenser and a nitrogen inlet tube, 15 g (43.7 mmol) of the above-obtained phthalonitrile (V-3), 6.65 g of 1,8-diazabicyclo[5.4.0]-7-undecene and 130 g of n-amyl alcohol were charged, followed by heating to 110° C. in a nitrogen atmosphere. At the same temperature, 1.3 g (13.1 mmol) of CuCl were added, followed by reaction at 110°–120° C. for 8 hours. After the completion of the reaction, the reaction mixture was cooled and insoluble matter was removed by filtration. The filtrate was concentrated under reduced pressure to distill off the solvent. The residue was purified by column chromatography, whereby 12.5 g of a mixture consisting of the target compound (I-3) and its isomer(s) were obtained. Physical properties and elemental analysis data of the compound so obtained are shown below:

Visible absorption:

$\lambda_{max} = 698$ nm $\epsilon g = 2.6 \times 10^5$ ml/g·cm (Solvent: toluene)

| Elemental analysis: $C_{80}H_{116}N_{12}O_8Cu$ | | | |
|---|---|---|---|
| | C | H | N |
| Calculated (%) | 66.88 | 8.08 | 11.70 |
| Found (%) | 66.82 | 8.13 | 11.71 |

Figure 7:
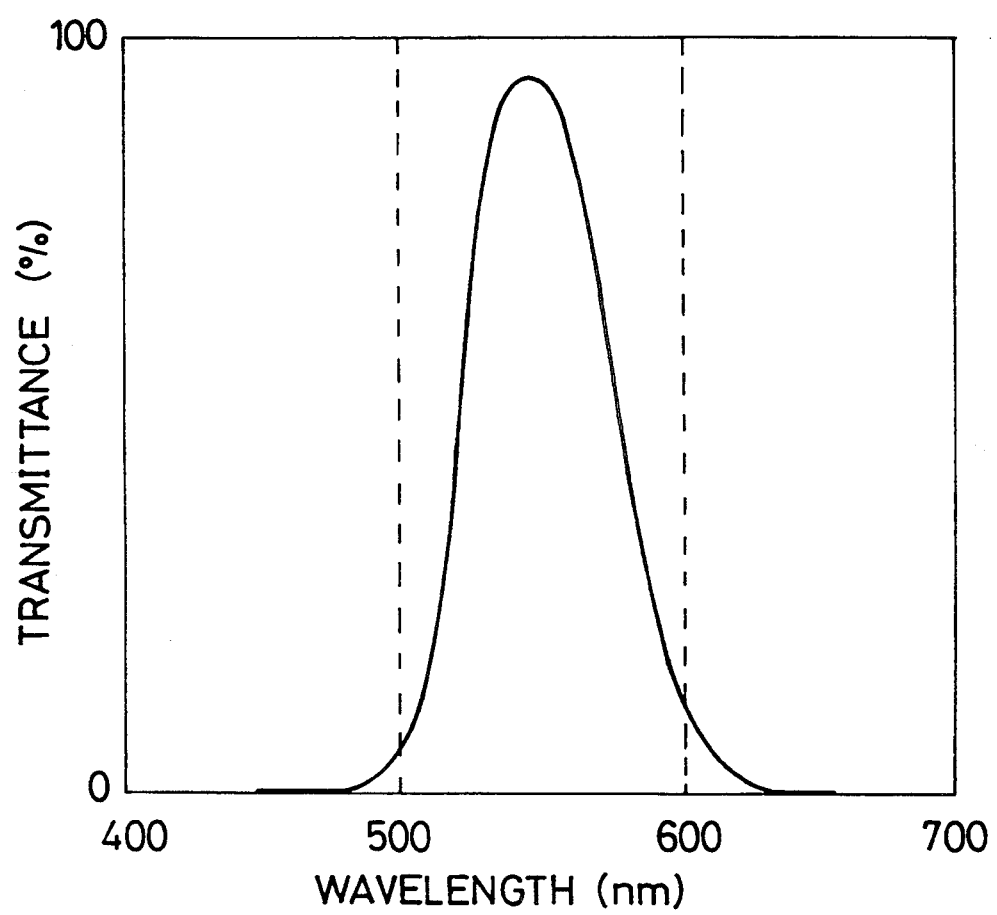

One gram of the phthalocyanine compound (I-3) and 1 g of "M/P yellow YL" (trade name; product of Mitsui Toatsu Dyes, Ltd.) were added to 100 g of polystyrene. The resulting resin composition was injection-molded, whereby a filter was fabricated. The filter so obtained was found to have not only good transmittance characteristics but also excellent durability. Its transmittance characteristics are shown in FIG. 7.

In addition, a solution (10 g/l) of the phthalocyanine compound (I-3) in n-octane was coated on a polycarbonate substrate, whereby an optical recording medium with gold as a reflective layer was fabricated. That optical recording medium showed 73% reflectance at 780–830 nm, and 62 dB sensitivity as measured on the basis of reflection of a 780 nm laser beam of 7 mW from its substrate at 1800 rpm.

Comparative Example 1

Figure 8:
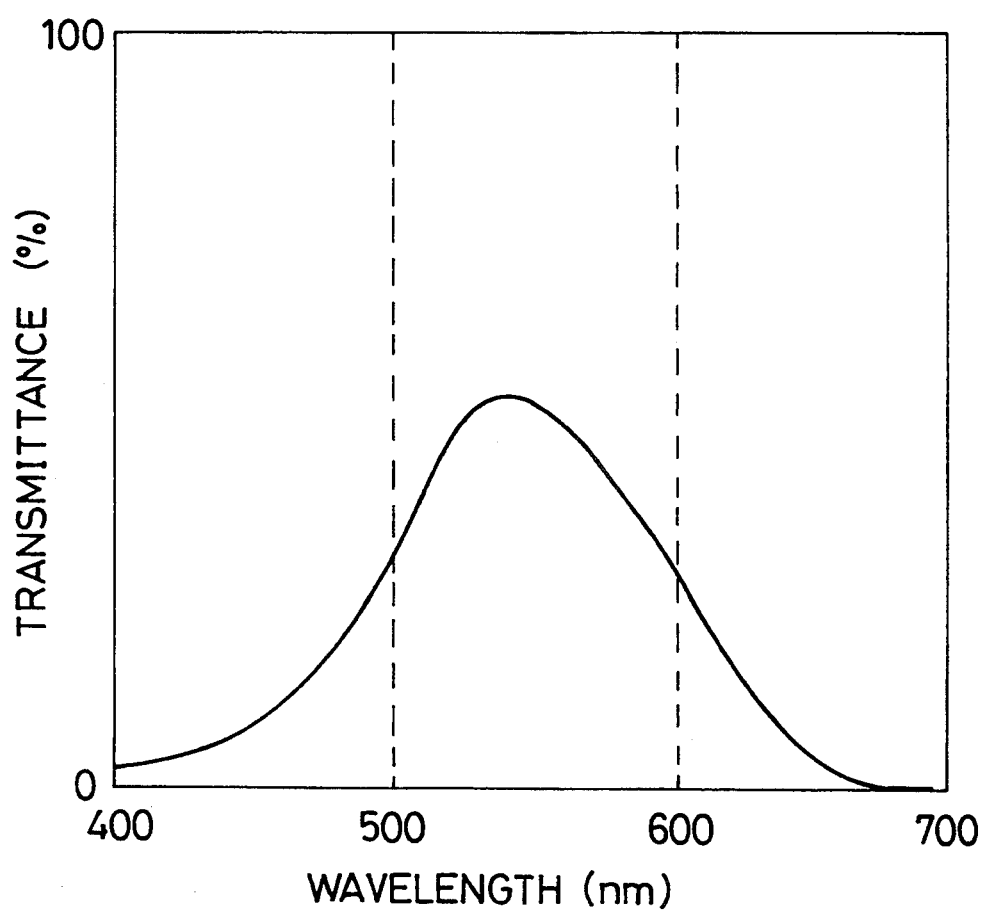

Using a known dye, a filter was fabricated in a similar manner to Example 1. Characteristics of the filter so obtained are shown in Table 2. In addition, transmittance characteristics of the filter are shown in FIG. 8.

Comparative Example 2

Figure 9:
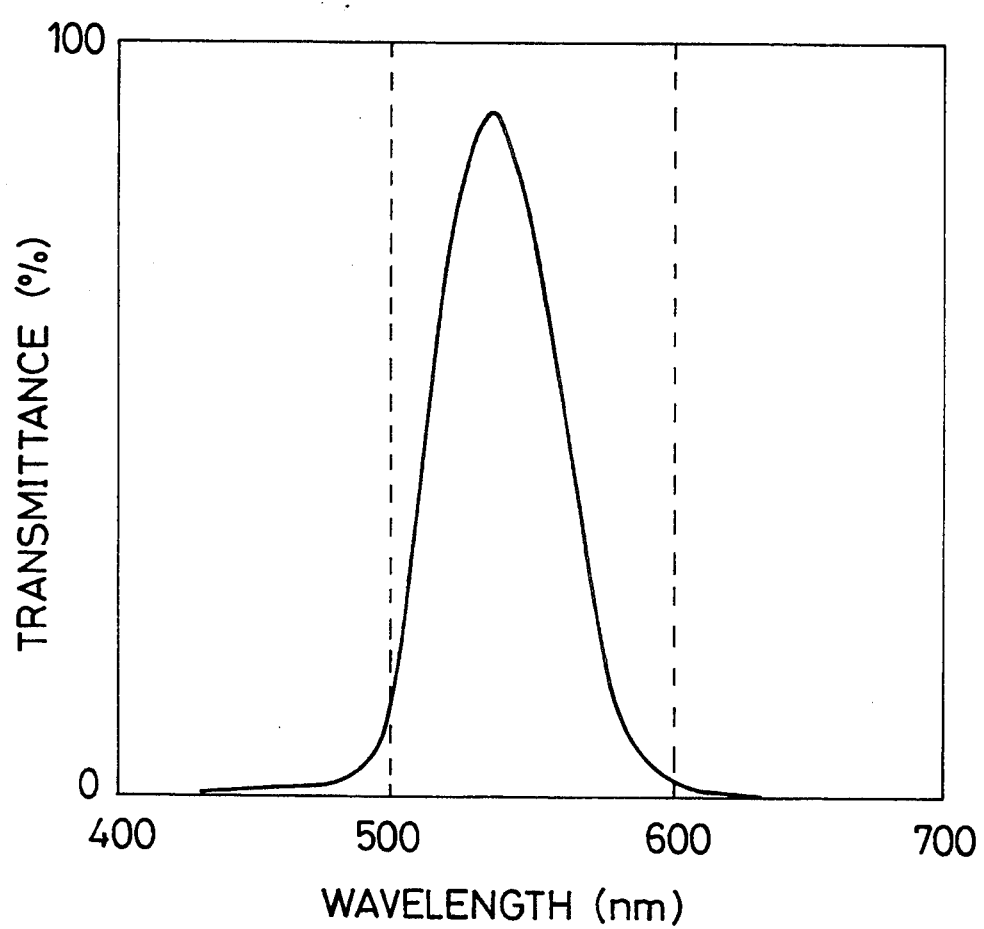

A filter was fabricated by coloring gelatin with a known dye. Characteristics of the filter so obtained are shown in Table 2. In addition, transmittance characteristics of the filter are shown in FIG. 9.

TABLE 2

| | Transmittance characteristics | Moisture resistance | Light resistance | Heat resistance |
|---|---|---|---|---|
| Example 1 | A (FIG. 5) | A | A | A |
| Example 2 | A (FIG. 6) | A | A | A |
| Comp. Ex. 1[1] | C (FIG. 8) | A | B | A |

TABLE 2-continued

| | Transmittance characteristics | Moisture resistance | Light resistance | Heat resistance |
|---|---|---|---|---|
| Comp. Ex. 2[2] | A (FIG. 9) | C | C | C |

[1] Employed was the dye disclosed in Japanese Patent Laid-Open No. 233401/1989 and having the following structural formula.

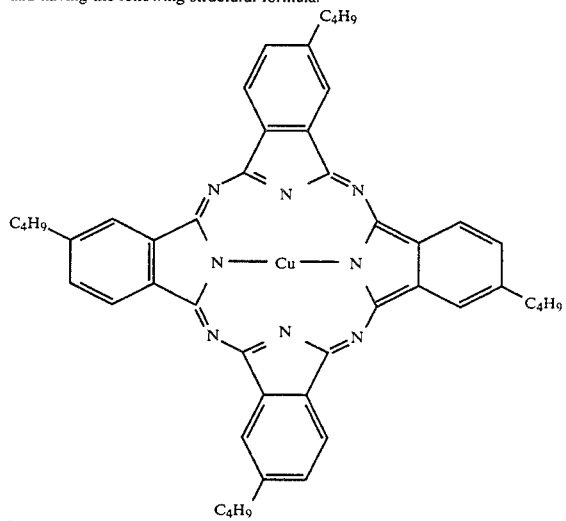

[2] Employed was "Acid Green 16", a dye described on page 48 of "Development Market Trend of Special Function Dyes in 1990's" published by CMC Press, Inc.

The following methods and standards were followed for the measurements of the respective characteristics and for the evaluation of the measurement results.

1. Transmittance characteristics

A: Maximum transmittance $\geq 80\%$, with the proviso that the transmittance is 10% or lower at (the wavelength for the maximum transmittance $\pm 50$) nm.

C: Maximum transmittance $\leq 70\%$, with the proviso that the transmittance is 10% or lower at (the wavelength for the maximum transmittance $\pm 50$) nm.

2. Moisture resistance

Color difference was determined after each filter was stored at 95% R.H. and 60° C. for 200 hours.

A: $\Delta E \leq 3$

C: $\Delta E \geq 5$

3. Light resistance

Color difference was determined after each filter was exposed to light from a fadeometer at 60° C. for 200 hours.

A: $\Delta E \leq 3$

B: $3 < \Delta E < 5$

C: $\Delta E \geq 5$

4. Heat resistance

Color difference was determined after each filter was stored at 250° C. for 1 hour.

A: $\Delta E \leq 3$

C: $\Delta E \geq 5$

Comparative Tests

Table 3 shows the maximum absorption wavelength ($\lambda_{max}$) of the compound obtained in each example and the molecular absorption coefficient (ε) of the compound at the maximum wavelength, both as measured in the form of a solution, and the solubility, maximum reflectance and sensitivity of the compound, in comparison with those of the known compounds to be described next.

Comparative Example 3

Compound No. 4 exemplified in Japanese Patent Laid-Open No. 152769/1986

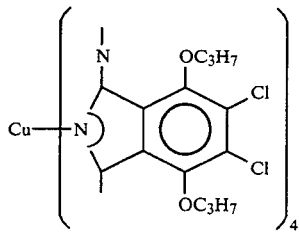

The above compound was dissolved in chloroform because of its insolubility in n-hexane. The resulting solution was coated on a polycarbonate substrate. The substrate so coated was evaluated as a medium.

Comparative Example 4

Compound described in Example 1 of Japanese Patent Laid-Open No. 209583/1985

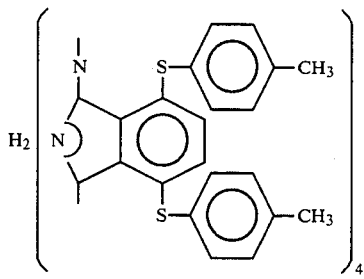

The above compound was dissolved in chloroform because of its insolubility in n-hexane. The resulting solution was coated on a polycarbonate substrate. The substrate so coated was evaluated as a medium.

Comparative Example 5

Compound No. 10 exemplified in Japanese Patent Laid-Open No. 197280/1986

Deca(—OC$_5$H$_{11}$)—H$_2$Pc

A solution of the above compound in carbon tetrachloride was coated on a polycarbonate plate. The substrate so coated was evaluated as a medium.

TABLE 3

|  | λ$_{max}$ (ε) | Solubility | Maximum reflectance (%) | Sensitivity |
| --- | --- | --- | --- | --- |
| Example 1 | 698 (2.5 × 10$^5$) | A | 42 | A |
| Example 2 | 698 (2.4 × 10$^5$) | A | 30 | A |
| Comp. Ex. 3 | 740 (1.5 × 10$^5$) | C | 24 | B |
| Comp. Ex. 4 | 780 (1.5 × 10$^5$) | C | 27 | B |
| Comp. Ex. 5 | 760 (1.5 × 10$^5$) | B | 20 | C |

The following methods and standards were followed for the measurements of the respective characteristics and for the evaluation of the measurement results.

1. Maximum absorption wavelength (λ$_{max}$) and molecular absorption coefficient (ε) at the wavelength Measured at a concentration of 5 mg/l in toluene or chloroform.

2. Solubility

A: Solubility of 5 g/l or more in n-hexane.

B: Solubility of less than 5 g/l in n-hexane but 5 g/l or more in carbon tetrachloride.

C: Solubility of less than 5 g/l in carbon tetrachloride.

3. Maximum reflectance (%)

The maximum reflectance is the reflectance obtained when a 5 g/l solution in n-hexane is coated on a polycarbonate substrate by a spin-coater and the substrate so obtained is then exposed to light of 780 nm.

4. Sensitivity

The sensitivity is expressed in terms of a C/N ratio as measured upon writing at a linear velocity of 5.5 m/sec with a 780 nm semiconductor laser beam of 8 mW.

A: C/N ≧ 40 (dB)

B: 40 > C/N ≧ 30 (dB)

C: C/N < 30 (dB)

EXAMPLE 4

In a vessel equipped with a stirrer, a reflux condenser and a nitrogen inlet tube, 10 g of 3-nitrophthalonitrile, 70 g of dried dimethylformamide (DMF) and 30 g of dried toluene were charged. They were thereafter converted completely into a solution, followed by cooling to 0° C. To the resulting solution, 100 g of a solution of 15.4 g of sodium oxide (the compound represented by the below-described formula VII-4), which had been prepared from sodium hydride, in DMF/toluene (7/3) was added dropwise at 0° to −5° C. After the temperature was raised to room temperature, the resulting solution was stirred for 2 hours. The target compound was obtained from the thus-obtained reaction mixture by extracting it with toluene and then purified by column chromatography, whereby 17 g of phthalonitrile (the compound represented by the below-described formula V-4) were obtained.

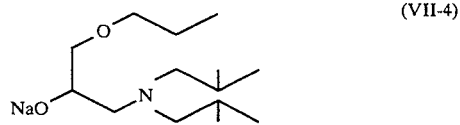 (VII-4)

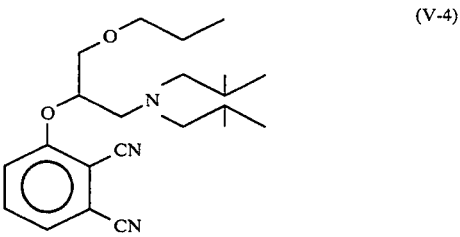 (V-4)

In a vessel equipped with a stirrer, a reflux condenser and a nitrogen inlet tube, 15 g (40.4 mmol) of the above-obtained phthalonitrile (V-4), 6.2 g of 1,8-diazabicyclo[5.4.0]-7-undecene and 100 g of n-amyl alcohol were charged, followed by heating to 110° C. in a nitrogen atmosphere. At the same temperature, 3.2 g (12.1 mmol) of VO(acac)₂ were added, followed by reaction at 110°-120° C. for 8 hours. After the completion of the reaction, the reaction mixture was cooled and insoluble matter was removed by filtration. The filtrate was concentrated under reduced pressure to distill off the solvent. The residue was purified by column chromatography, whereby 13 g of a mixture consisting of the target compound (I-4) and its isomer(s) were obtained. Physical properties and elemental analysis data of the compound so obtained are shown below:

Visible absorption:
$\lambda_{max}$ = 725 nm
$\epsilon g = 2.3 \times 10^5$ ml/g·cm
(Solvent: toluene)

| Elemental analysis: $C_{88}H_{132}N_{12}O_9V$ | | | |
|---|---|---|---|
| | C | H | N |
| Calculated (%) | 68.09 | 8.51 | 10.83 |
| Found (%) | 68.08 | 8.53 | 10.82 |

One gram of the phthalocyanine compound (I-4) was added to 100 g of polystyrene. The resulting resin composition was injection-molded, whereby a filter was fabricated. The filter so obtained was found to have not only good transmittance characteristics but also excellent durability.

In addition, a solution (10 g/l) of the phthalocyanine compound (I-4) in n-octane was coated on a polycarbonate substrate, whereby an optical recording medium with gold as a reflective layer was fabricated. That optical recording medium showed 71% reflectance at 780-830 nm, and 64 dB sensitivity as measured on the basis of reflection of a 780 nm laser beam of 7 mW from its substrate at 1800 rpm.

EXAMPLE 5

In a vessel equipped with a stirrer, a reflux condenser and a nitrogen inlet tube, 10 g of 3-nitrophthalonitrile, 70 g of dried dimethylformamide (DMF) and 30 g of dried toluene were charged. They were thereafter converted completely into a solution, followed by cooling to 0° C. To the resulting solution, 100 g of a solution of 18.6 g of sodium oxide (the compound represented by the below-described formula VII-5), which had been prepared from sodium hydride, in DMF/toluene (7/3) was added dropwise at 0° to −5° C. After the temperature was raised to room temperature, the resulting solution was stirred for 2 hours. The target compound was obtained from the thus-obtained reaction mixture by extracting it with toluene and then purified by column chromatography, whereby 18 g of phthalonitrile (the compound represented by the below-described formula V-5) were obtained.

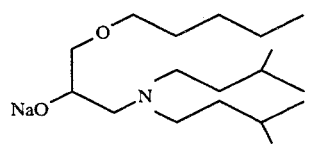

(VII-5)

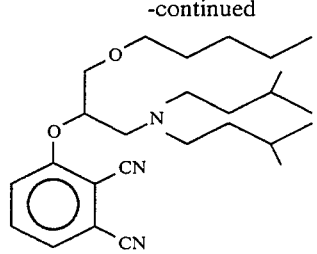

(V-5)

In a vessel equipped with a stirrer, a reflux condenser and a nitrogen inlet tube, 15 g (35.1 mmol) of the above-obtained phthalonitrile (V-5), 5.34 g of 1,8-diazabicyclo[5.4.0]-7-undecene and 120 g of n-amyl alcohol were charged, followed by heating to 110° C. in a nitrogen atmosphere. At the same temperature, 1.04 g (10.5 mmol) of CuCl were added, followed by reaction at 110°-120° C. for 8 hours. After the completion of the reaction, the reaction mixture was cooled and insoluble matter was removed by filtration. The filtrate was concentrated under reduced pressure to distill off the solvent. The residue was purified by column chromatography, whereby 13 g of a mixture consisting of the target compound (I-5) and its isomer(s) were obtained. Physical properties and elemental analysis data of the compound so obtained are shown below:

Visible absorption:
$\lambda_{max}$ = 700 nm
$\epsilon g = 2.6 \times 10^5$ ml/g·cm
(Solvent: toluene)

| Elemental analysis: $C_{104}H_{164}N_{12}O_8Cu$ | | | |
|---|---|---|---|
| | C | H | N |
| Calculated (%) | 70.45 | 9.26 | 9.48 |
| Found (%) | 70.30 | 9.32 | 9.45 |

Mixed into a homogeneous solution were 122 g of 1,4-bis(α,α-dimethylisocyanatomethyl)benzene, 117 g of 1,3,5-tris(3-mercaptopropyl)isocyanurate, 10 g of the compound (I-5) and 0.3 g of dibutyltin dilaurate. The solution was poured into a mold formed of glasses, which had been subjected to surface treatment with a fluorine-base external mold releasing agent, with PVC gasket.

After heated at 70° C. for 4 hours, at 80° C. for 2 hours, at 90° C. for 2 hours, at 100° C. for 2 hours and at 120° C. for 2 hours, the mold was cooled and the filter so molded was released. The filter exhibited good transmittance characteristics and were also excellent in light resistance and moisture resistance.

In addition, a solution (10 g/l) of the phthalocyanine compound (I-5) in n-octane was coated on a polycarbonate substrate, whereby an optical recording medium with gold as a reflective layer was fabricated. That optical recording medium showed 73% reflectance at 780-830 nm, and 61 dB sensitivity as measured on the basis of reflection of a 780 nm laser beam of 7 mW from its substrate at 1800 rpm.

EXAMPLE 6

In a vessel equipped with a stirrer, a reflux condenser and a nitrogen inlet tube, 10 g of 6-chloro-3-nitrophthalonitrile, 70 g of dried dimethylformamide (DMF) and 30 g of dried toluene were charged. They were thereafter converted completely into a solution, followed by cooling to 0° C. To the resulting solution, 100 g of a solution of 10.2 g of sodium oxide (the compound represented by the below-described formula VII-6), which had been prepared from sodium hydride, in DMF/toluene (7/3) was added dropwise at 0° to −5° C. After the temperature was raised to room temperature, the resulting solution was stirred for 2 hours. The target compound was obtained from the thus-obtained reaction mixture by extracting it with toluene and then purified by column chromatography, whereby 13 g of phthalonitrile (the compound represented by the below-described formula V-6) were obtained.

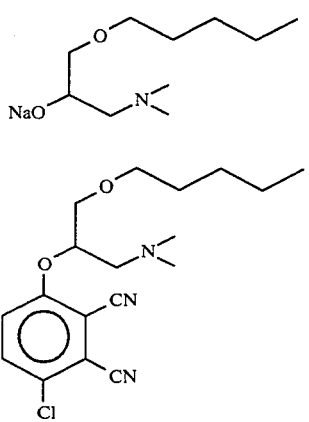

In a vessel equipped with a stirrer, a reflux condenser and a nitrogen inlet tube, 10 g (28.6 mmol) of the above-obtained phthalonitrile (V-6), 4.3 g of 1,8-diazabicy-clo[5.4.0]-7-undecene and 100 g of n-amyl alcohol were charged, followed by heating to 110° C. in a nitrogen atmosphere. At the same temperature, 1.08 g (8.5 mmol) of $FeCl_2$ were added, followed by reaction at 110°-120° C. for 8 hours. After the completion of the reaction, the reaction mixture was cooled and insoluble matter was removed by filtration. The filtrate was concentrated under reduced pressure to distill off the solvent. The residue was purified by column chromatography, whereby 8.1 g of a mixture consisting of the target compound (I-6) and its isomer(s) were obtained. Physical properties and elemental analysis data of the compound so obtained are shown below:

Visible absorption:
$\lambda_{max} = 707$ nm
$\epsilon g = 2.3 \times 10^5$ ml/g·cm
(Solvent: toluene)

| Elemental analysis: $C_{72}H_{96}N_{12}O_8Cl_4Fe$ | | | |
|---|---|---|---|
| | C | H | N |
| Calculated (%) | 59.43 | 6.60 | 11.56 |
| Found (%) | 59.42 | 6.62 | 11.57 |

A solution (10 g/l) of the phthalocyanine compound (I-6) in n-octane was coated on a polycarbonate substrate, whereby an optical recording medium with gold as a reflective layer was fabricated. That optical recording medium showed 72% reflectance at 780–830 nm, and 65 dB sensitivity as measured on the basis of reflection of a 780 nm laser beam of 7 mW from its substrate at 1800 rpm.

In addition, 100 g of polymethyl methacrylate and 3 g of the compound (I-6) were dissolved in 500 g of chloroform. The resulting solution was cast on a glass substrate and was then dried. The filter so fabricated was found to have good durability and filtering characteristics.

EXAMPLE 7

In a vessel equipped with a stirrer, a reflux condenser and a nitrogen inlet tube, 10 g of 4,6-dibromo-3-nitroph-thalonitrile, 70 g of dried dimethylformamide (DMF) and 30 g of dried toluene were charged. They were thereafter converted completely into a solution, followed by cooling to 0° C. To the resulting solution, 100 g of a solution of 7.3 g of sodium oxide (the compound represented by the below-described formula VII-7), which had been prepared from sodium hydride, in DMF/toluene (7/3) was added dropwise at 0° to −5° C. After the temperature was raised to room temperature, the resulting solution was stirred for 2 hours. The target compound was obtained from the thus-obtained reaction mixture by extracting it with toluene and then purified by column chromatography, whereby 13 g of phthalonitrile (the compound represented by the below-described formula V-7) were obtained.

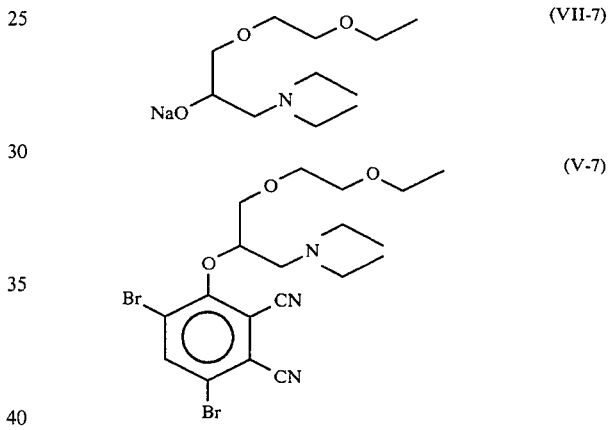

In a vessel equipped with a stirrer, a reflux condenser and a nitrogen inlet tube, 12 g (23.9 mmol) of the above-obtained phthalonitrile (V-7), 3.6 g of 1,8-diazabicy-clo[5.4.0]-7-undecene and 100 g of n-amyl alcohol were charged, followed by heating to 110° C. in a nitrogen atmosphere. At the same temperature, 0.71 g (7.2 mmol) of CuCl was added, followed by reaction at 110°-120° C. for 8 hours. After the completion of the reaction, the reaction mixture was cooled and insoluble matter was removed by filtration. The filtrate was concentrated under reduced pressure to distill off the solvent. The residue was purified by column chromatography, whereby 11 g of a mixture consisting of the target compound (I-7) and its isomer(s) were obtained. Physical properties and elemental analysis data of the compound so obtained are shown below:

Visible absorption:
$\lambda_{max} = 710$ nm
$\epsilon g = 2.5 \times 10^5$ ml/g·cm
(Solvent: toluene)

| Elemental analysis: $C_{76}H_{100}N_{12}O_{12}Br_8Cu$ | | | |
|---|---|---|---|
| | C | H | N |
| Calculated (%) | 14.96 | 4.82 | 8.10 |
| Found (%) | 43.98 | 4.85 | 8.11 |

One gram of the phthalocyanine compound (I-7) was added to 100 g of polystyrene. The resulting resin composition was injection-molded, whereby a filter was fabricated. The filter so obtained was found to have not only good transmittance characteristics but also have excellent durability.

In addition, a solution (10 g/l) of the phthalocyanine compound (I-7) in n-octane was coated on a polycarbonate substrate, whereby an optical recording medium with gold as a reflective layer was fabricated. That optical recording medium showed 72% reflectance at 780–830 nm, and 63 dB sensitivity as measured on the basis of reflection of a 780 nm laser beam of 7 mW from its substrate at 1800 rpm.

EXAMPLE 8

In a vessel equipped with a stirrer, a reflux condenser and a nitrogen inlet tube, 10 g of 3-nitrophthalonitrile, 70 g of dried dimethylformamide (DMF) and 30 g of dried toluene were charged. They were thereafter converted completely into a solution, followed by cooling to 0° C. To the resulting solution, 100 g of a solution of 15.6 g of sodium oxide (the compound represented by the below-described formula VII-8), which had been prepared from sodium hydride, in DMF/toluene (7/3) was added dropwise at 0° to −5° C. After the temperature was raised to room temperature, the resulting solution was stirred for 2 hours. The target compound was obtained from the thus-obtained reaction mixture by extracting it with toluene and then purified by column chromatography, whereby 18 g of phthalonitrile (the compound represented by the below-described formula V-8) were obtained.

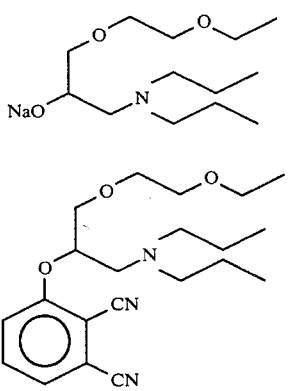

(VII-8)

(V-8)

In a vessel equipped with a stirrer, a reflux condenser and an ammonia gas inlet tube, 15 g of the above-obtained phthalonitrile (V-8), 100 g of methanol and 1.1 g of sodium methylate were charged, followed by the blowing of ammonia gas at a molar ratio of 6.4 times relative to the compound V-8. After the contents were heated to 55°–60° C., they were reacted under heating for 2 hours. Methanol was thereafter distilled off under reduced pressure and organic substance was extracted with toluene. Hexane was added to precipitate crystals, whereby 14 g of the target compound (VI-1) were obtained.

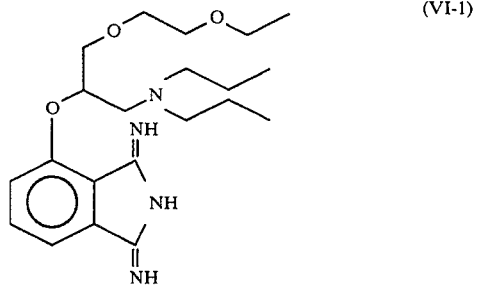

(VI-1)

A mixture consisting of 2.3 g of FeCl$_2$ and 100 g of quinoline was heated to 200° C. To the mixture, 10 g of the above-obtained diiminoisoindoline derivative (VI-1) were added, followed by heating under reflux for 5 hours. The reaction mixture was poured into 500 g of methanol. After suction filtration, crystals so collected were washed with methanol, followed by drying, whereby 8.2 g of a mixture consisting of the compound (I-8) and its isomer(s) were obtained. Physical properties and elemental analysis data of the compound so obtained are shown below.

Visible absorption:
$\lambda_{max} = 708$ nm
$\epsilon g = 2.6 \times 10^5$ ml/g·cm
(Solvent: toluene)

| Elemental analysis: $C_{84}H_{124}N_{12}O_{12}Fe$ | | | |
|---|---|---|---|
| | C | H | N |
| Calculated (%) | 65.12 | 8.01 | 10.85 |
| Found (%) | 65.10 | 8.03 | 10.90 |

In 100 g of dibutyl ether, 1 g of the phthalocyanine compound (I-8) was dissolved. The resulting solution was coated on a polycarbonate substrate for optical disc. The optical disc thus fabricated was found to have a reflectance of 36% and a sensitivity of 51 dB in terms of C/N ratio as measured at a linear velocity of 5.5 m/sec by a 780 nm laser beam of 8 mW.

In addition, a solution of 1 g of the phthalocyanine compound (I-8) in 100 g of dibutyl ether was coated on the polycarbonate substrate for optical card and the surface of the recording layer was coated with a resin, whereby an optical card was fabricated. That optical card was found to have a reflectance of 36% and a sensitivity of 53 dB in terms of C/N ratio as measured at a linear velocity of 2.8 m/sec by a 780 nm laser beam of 8 mW.

EXAMPLE 9

In a vessel equipped with a stirrer, a reflux condenser and a nitrogen inlet tube, 10 g of 4,5-diphenylthio-3-nitrophthalonitrile, 70 g of dried dimethylformamide (DMF) and 30 g of dried toluene were charged. They were thereafter converted completely into a solution, followed by cooling to 0° C. To the resulting solution, 100 g a solution of 7.6 g of sodium oxide (the compound represented by the below-described formula VII-9), which had been prepared from sodium hydride, in DMF/toluene (7/3) was added dropwise at 0° to −5° C. After the temperature was raised to room temperature, the resulting solution was stirred for 2 hours. The target compound was obtained from the thus-obtained reaction mixture by extracting it with toluene and then purified by column chromatography, whereby 15 g of phthalonitrile (the compound represented by the below-described formula V-9) were obtained.

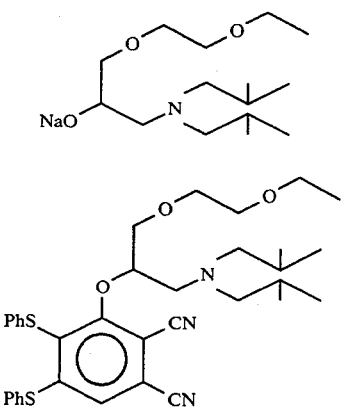

(VII-9)

(V-9)

In a vessel equipped with a stirrer, a reflux condenser and a nitrogen inlet tube, 15 g (24.3 mmol) of the above-obtained phthalonitrile (V-9), 3.7 g of 1,8-diazabicyclo[5.4.0]-7-undecene and 100 g of chloronaphthalene were charged, followed by heating to 110° C. in a nitrogen atmosphere. At the same temperature, 0.72 g (7.3 mmol) of CuCl was added, followed by reaction at 110°-120° C. for 8 hours. After the completion of the reaction, the reaction mixture was cooled and insoluble matter was removed by filtration. The filtrate was concentrated under reduced pressure to distill off the solvent. The residue was purified by column chromatography, whereby 11 g of a mixture consisting of the target compound (I-9) and its isomer(s) were obtained. Physical properties and elemental analysis data of the compound so obtained are shown below:

Visible absorption:
$\lambda_{max} = 745$ nm
$\epsilon g = 2.6 \times 10^5$ ml/g·cm
(Solvent: toluene)

| Elemental analysis: $C_{140}H_{172}N_{12}O_{12}S_8Cu$ | | | |
|---|---|---|---|
| | C | H | N |
| Calculated (%) | 66.36 | 6.79 | 6.64 |
| Found (%) | 66.32 | 6.80 | 6.67 |

In 10 g of a photoresist ("TPR", trade name; product of Tokyo Ohka Kogyo Co., Ltd.), 5 g of the above-obtained phthalocyanine compound (I-9) and 5 g of "M/P yellow F3G" (trade name; product of Mitsui Toatsu Dyes, Ltd.) were dissolved. A glass substrate was spin-coated with the resultant coating formulation by using a spinner. The substrate was prebaked at 85°-100° C. for 2-5 minutes and then exposed (20-30 mj/cm², 2 min.) to light from a high-pressure mercury lamp via a mask having a striped pattern. The resulting substrate was developed so that a pattern was formed thereon. Finally, the substrate was post-baked at 200°-230° C. for 10-30 minutes, whereby a filter with green stripes was obtained. The thickness of the dye layer was 2 μm.

The filter so obtained was superior in durability (moisture resistance, light resistance and heat resistance) and also in transmittance characteristics.

In addition, a solution (10 g/l) of the phthalocyanine compound (I-9) in n-octane was coated on a polycarbonate substrate, whereby an optical recording medium with gold as a reflective layer was fabricated. That optical recording medium showed 70% reflectance at 780-830 nm, and 60 dB sensitivity as measured on the basis of reflection of a 780 nm laser beam of 7 mW from its substrate at 1800 rpm.

EXAMPLE 10-50

In each example, one to four of the phthalonitriles represented by the below-described formula (V) (Table 4) or of the diiminoisoindolines represented by the below-described formula (VI) (Table 5) were reacted with a metal derivative under the conditions shown in Table 6, whereby a phthalocyanine compound and its isomer(s) were both synthesized. A filter fabricated using the thus-obtained compound was found to be excellent in both transmittance characteristics and durability. In addition, an optical recording medium fabricated using the compound was found to have good reflectance, sensitivity and durability.

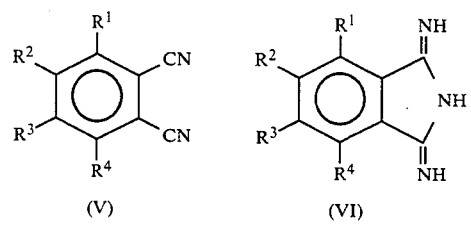

(V)  (VI)

TABLE 4

| Intermediate | $R^1$ | $R^2$ | $R^3$ | $R^4$ |
|---|---|---|---|---|
| V-10 | (structure) | H | H | H |
| V-11 | (structure) | H | H | H |

TABLE 4-continued

| Intermediate | R¹ | R² | R³ | R⁴ |
|---|---|---|---|---|
| V-12 | (structure) | H | H | H |
| V-13 | (structure) | H | H | H |
| V-14 | (structure) | H | H | H |
| V-15 | (structure) | Cl | Cl | (structure) |
| V-16 | (structure) | H | H | (structure) |
| V-17 | (structure) | Cl | H | (structure) |
| V-18 | (structure) | I | I | H |
| V-19 | (structure) | I | H | Br |
| V-20 | (structure) | Br | Br | H |
| V-21 | (structure) | Br | Br | Br |
| V-22 | (structure) | H | H | H |

TABLE 4-continued

| Intermediate | R[1] | R[2] | R[3] | R[4] |
|---|---|---|---|---|
| V-23 | (structure) | S—CH$_3$ | S—CH$_3$ | H |
| V-24 | (structure) | SPh | SPh | H |
| V-25 | (structure) | H | H | H |
| V-26 | (structure) | Br | Br | H |
| V-27 | (structure) | Cl | Cl | Cl |
| V-28 | (structure) | H | H | H |
| V-29 | (structure) | —S—C$_6$H$_4$—Cl | —S—C$_6$H$_4$—Cl | (structure) |
| V-30 | (structure) | H | H | (structure) |
| V-31 | (structure) | H | Br | H |
| V-32 | (structure) | H | H | Br |
| V-33 | (structure) | H | I | H |
| V-34 | (structure) | H | H | (structure) |
| V-35 | (structure) | SPh | SPh | (structure) |
| V-36 | (structure) | H | H | H |

TABLE 4-continued

| Intermediate | R¹ | R² | R³ | R⁴ |
|---|---|---|---|---|
| V-37 | -O-CH₂CH₂-N=CH-C(CH₃)= (ether-linked imine with methyl branch) | Br | Br | Br |
| V-38 | -O-CH₂CH₂-N=CH-C(CH₃)= | H | H | -O-CH₂CH₂-N=CH-C(CH₃)= |
| V-39 | -CH₂-N=CH-C(CH₃)= | Cl | H | H |
| V-40 | -CH₂-N=CH-C(CH₃)=C(CH₃) | H | H | -CH₂-N=CH-C(CH₃)=CH-CH₃ |

TABLE 5

| Intermediate | R¹ | R² | R³ | R⁴ |
|---|---|---|---|---|
| VI-2 | -S-CH(CH₂SC₂H₅)-CH₂-N(CH₃)₂ | H | H | H |
| VI-3 | -S-CH(CH₂SC₂H₅)-CH₂-N=CH₂ | H | H | H |
| VI-4 | -S-CH(CH₂SC₂H₅)-CH₂-N=CH-CH=CH₂ | H | H | H |
| VI-5 | -S-CH(CH₂SC₂H₅)-CH₂-N=CH-C(CH₃)= | H | H | H |
| VI-6 | -S-CH(CH₂S-C₄H₉)-CH₂-N=CH-CH=CH-CH₃ | H | H | H |
| VI-7 | -S-CH(CH₂S-C₄H₉)-CH₂-N(CH₃)- | H | H | H |
| VI-8 | -S-CH(CH₂SCH₂CH₂SC₂H₅)-CH₂-N=CH₂ | H | H | H |
| VI-9 | -S-CH(CH₂SCH₂CH₂SC₂H₅)-CH₂-N=CH-CH=CH₂ | H | H | H |
| VI-10 | -S-CH(CH₂SCH₂CH₂SC₂H₅)-CH₂-N=CH-C(CH₃)= | H | H | H |
| VI-11 | -S-CH(CH₂SCH₂CH₂SC₂H₅)-CH₂-N=CH-C(CH₃)=CH-CH₃ | H | H | H |

TABLE 6

| Cmp'd | Metal | Preparation process | $\lambda_{max}$ |
|---|---|---|---|
| I-10 | Cu | Reaction of CuCl, the intermediate (V-10) and DBU in amyl alcohol | 699 |
| I-11 | Co | Reaction of COCl₂, the intermediate (V-11) and DBU in amyl alcohol | 693 |
| I-12 | Cu | Reaction of CuCl, the intermediate (V-12) and DBU in amyl alcohol | 700 |
| I-13 | Cu | Reaction of CuCl, the intermediate (V-13) and DBU in amyl alcohol | 699 |
| I-14 | Zn | Reaction of Zn(OAc)₂, the intermediate (V-14) and DBU in amyl alcohol | 702 |
| I-15 | Cu | Reaction of CuCl, the intermediate (V-15) and DBU in amyl alcohol | 770 |
| I-16 | Fe | Reaction of FeCl₂, the intermediate (V-16) and DBU in amyl alcohol | 758 |
| I-17 | Fe | Reaction of FeCl₂, the intermediate (V-17) and DBU in amyl alcohol | 765 |
| I-18 | VO | Reaction of VO(acac)₂, the intermediate (V-18) and DBU in amyl alcohol | 720 |
| I-19 | VO | Reaction of VO(acac)₂, the intermediate (V-19) and DBU in amyl alcohol | 725 |
| I-20 | Cu | Reaction of CuCl, the intermediate (V-20) and DBU in amyl alcohol | 705 |
| I-21 | Co | Reaction of CoCl₂, the intermediate (V-21) and DBU in amyl alcohol | 710 |
| I-22 | InCl | Reaction of InCl₃, the intermediate (V-22) and DBU in amyl alcohol | 720 |
| I-23 | Cu | Reaction of CuCl, the intermediate (V-23) and DBU in amyl alcohol | 745 |
| I-24 | Cu | Reaction of CuCl, the | 750 |

TABLE 6-continued

| Cmp'd | Metal | Preparation process | $\lambda_{max}$ |
|---|---|---|---|
| I-25 | Mn | Reaction of MnCl$_2$, the intermediate (V-24) and DBU in amyl alcohol | 685 |
| I-26 | Co | Reaction of CoCl$_2$, the intermediate (V-25) and DBU in amyl alcohol | 715 |
| I-27 | Fe | Reaction of FeCl$_2$, the intermediate (V-26) and DBU in chloronaphthalene | 705 |
| I-28 | Zn | Reaction of Zn(OAc)$_2$, the intermediate (V-27) and DBU in chloronaphthalene | 710 |
| I-29 | Cu | Reaction of CuCl, the intermediate (V-28) and DBU in chloronaphthalene | 790 |
| I-30 | Zn | Reaction of Zn(OAc)$_2$, the intermediate (V-29) and DBU in chloronaphthalene | 745 |
| I-31 | Cu | Reaction of CuCl, the intermediate (V-30) and DBU in chloronaphthalene | 705 |
| I-32 | Cu | Reaction of CuCl, the intermediate (V-31) and DBU in chloronaphthalene | 706 |
| I-33 | Pd | Reaction of PdCl$_2$, the intermediate (V-32) and DBU in chloronaphthalene | 695 |
| I-34 | SiCl$_2$ | Reaction of SiCl$_4$, the intermediate (V-33) and DBU in amyl alcohol | 750 |
| I-35 | Pb | Reaction of Pb(OAc)$_2$, the intermediate (V-34) and DBU in amyl alcohol | 797 |
| I-36 | Cu | Reaction of CuCl, the intermediate (V-35) and DBU in amyl alcohol | 760 |
| I-37 | Cu | Reaction of CuCl, the intermediate (V-36) and DBU in amyl alcohol | 720 |
| I-38 | VO | Reaction of VO(acac)$_2$, the intermediate (V-37) and DBU in amyl alcohol | 775 |
| I-39 | Fe | Reaction of FeCl$_2$, the intermediate (V-38) and DBU in chloronaphthalene | 685 |
| I-40 | Cu | Reaction of CuCl, the intermediate (V-39) and DBU in amyl alcohol | 687 |
| I-41 | Cu | Reaction of CuCl and the intermediate (VI-2) in quinoline | 702 |
| I-42 | Cu | Reaction of CuCl and the intermediate (VI-3) in quinoline | 703 |
| I-43 | Cu | Reaction of CuCl and the intermediate (VI-4) in quinoline | 702 |
| I-44 | Co | Reaction of CoCl$_2$ and the intermediate (VI-5) in quinoline | 700 |
| I-45 | Cu | Reaction of CuCl and the intermediate (VI-6) in quinoline | 703 |
| I-46 | Fe | Reaction of FeCl$_2$ and the intermediate (VI-7) in quinoline | 710 |
| I-47 | Fe | Reaction of FeCl$_2$ and the intermediate (VI-8) in quinoline | 711 |
| I-48 | Cu | Reaction of CuCl and the intermediate (VI-9) in quinoline | 703 |
| I-49 | VO | Reaction of VO(acac)$_2$ and the intermediate (VI-10) in quinoline | 720 |
| I-50 | InCl | Reaction of InCl$_3$ and the intermediate (VI-11) in quinoline | 715 |

"acac" represents $$\underset{\ominus}{\overset{O\quad\quad O}{\underset{\|\quad\quad\|}{\diagup\diagdown\diagup\diagdown}}}$$

EXAMPLE 51

In a vessel equipped with a stirrer, a reflux condenser and a nitrogen inlet tube, 10 g of 3-nitrophthalonitrile, 70 g of dried dimethylformamide (DMF) and 30 g of dried toluene were charged. They were thereafter converted completely into a solution, followed by cooling to 0° C. To the resulting solution, 100 g of a solution of 22.5 g of sodium sulfide (the compound represented by the below-described formula VII-10), which had been prepared from sodium hydride, in DMF/toluene (7/3) was added dropwise at 0° to −5° C. After the temperature was raised to room temperature, the resulting solution was stirred for 2 hours. The target compound was obtained from the thus-obtained reaction mixture by extracting it with toluene and then purified by column chromatography, whereby 19 g of phthalonitrile (the compound represented by the below-described formula V-41) were obtained.

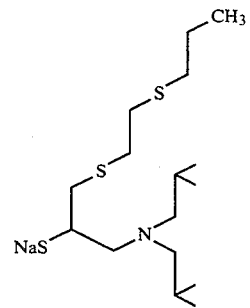

(VII-10)

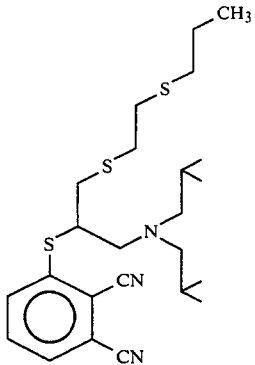

(V-41)

In a vessel equipped with a stirrer, a reflux condenser and a nitrogen inlet tube, 15.5 g (31.3 mmol) of the above-obtained phthalonitrile (V-41), 4.8 g of 1,8-diazabicyclo[5.4.0]-7-undecene and 100 g of n-amyl alcohol were charged, followed by heating to 110° C. in a nitrogen atmosphere. At the same temperature, 1.6 g (9.4 mmol) of SiCl$_4$ were added, followed by reaction at 110°–120° C. for 8 hours. After the completion of the reaction, the reaction mixture was cooled and insoluble matter was removed by filtration. The filtrate was concentrated under reduced pressure to distill off the solvent. The residue was purified by column chromatography, whereby 10.5 g of a mixture consisting of the target compound (I-51) and its isomer(s) were obtained. Physical properties and elemental analysis data of the compound so obtained are shown below:

Visible absorption:
$\lambda_{max}$=710 nm
$\epsilon g = 2.3 \times 10^5$ ml/g·cm
(Solvent: toluene)

| Elemental analysis: $C_{96}H_{148}N_{12}S_{16}Cl_2Si$ | | | |
|---|---|---|---|
| | C | H | N |
| Calculated (%) | 55.41 | 7.12 | 8.08 |

-continued

| Elemental analysis: $C_{96}H_{148}N_{12}S_{16}Cl_2Si$ | | | |
|---|---|---|---|
| | C | H | N |
| Found (%) | 55.40 | 7.15 | 8.09 |

In 10 g of a prepolymer ("SD-17", trade name; product of Dainippon Ink & Chemicals, Inc.), 1 g of the above-obtained phthalocyanine compound (I-51) and 1 g of "M/P yellow 3GSL" (trade name; product of Mitsui Toatsu Dyes, Ltd.) were dissolved. A glass substrate was spin-coated with the resultant coating formulation by using a spinner. After being dried, the substrate was prebaked at 85°–100° C. for 2–5 minutes and then exposed (20–30 mj/cm², 2 min.) to light from a high-pressure mercury lamp via a mask having a striped pattern. The resulting substrate was developed so that a pattern was formed thereon. Finally, the substrate was postbaked at 200°–230° C. for 10–30 minutes, whereby a filter with green stripes was obtained. The thickness of the dye layer was 1 μm.

The filter so obtained was superior in durability (moisture resistance, light resistance and heat resistance) and also in transmittance characteristics.

In addition, a solution (10 g/l) of the phthalocyanine compound (I-51) in n-octane was coated on a polycarbonate substrate, whereby an optical recording medium with gold as a reflective layer was fabricated. That optical recording medium showed 73% reflectance at 780–830 nm, and 58 dB sensitivity as measured on the basis of reflection of a 780 nm laser beam of 7 mW from its substrate at 1800 rpm.

EXAMPLE 52

In a vessel equipped with a stirrer, a reflux condenser and a nitrogen inlet tube, 10 g of 3-nitrophthalonitrile, 70 g of dried dimethylformamide (DMF) and 30 g of dried toluene were charged. They were thereafter converted completely into a solution, followed by cooling to 0° C. To the resulting solution, 100 g of a solution of 20.9 g of sodium sulfide (the compound represented by the below-described formula VII-11), which had been prepared from sodium hydride, in DMF/toluene (7/3) was added dropwise at 0° to −5° C. After the temperature was raised to room temperature, the resulting solution was stirred for 2 hours. The target compound was obtained from the thus-obtained reaction mixture by extracting it with toluene and then purified by column chromatography, whereby 18.5 g of phthalonitrile (the compound represented by the below-described formula V-42) were obtained.

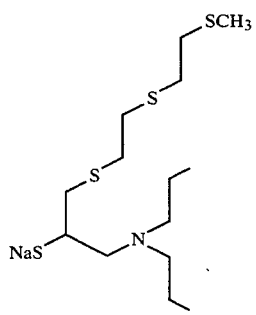

(VII-11)

-continued

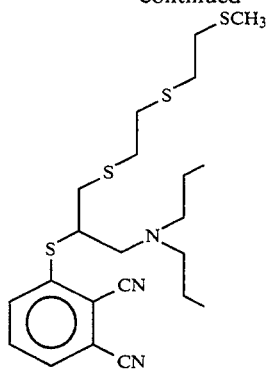

(V-42)

In a vessel equipped with a stirrer, a reflux condenser and a nitrogen inlet tube, 15 g (32.3 mmol) of the above-obtained phthalonitrile (V-42), 4.9 g of 1,8-diazabicyclo[5.4.0]-7-undecene and 110 g of n-amyl alcohol were charged, followed by heating to 110° C. in a nitrogen atmosphere. At the same temperature, 1.78 g (9.7 mmol) of Zn(OAc)₂ were added, followed by reaction at 110°–120° C. for 8 hours. After the completion of the reaction, the reaction mixture was cooled and insoluble matter was removed by filtration. The filtrate was concentrated under reduced pressure to distill off the solvent. The residue was purified by chromatography, whereby 13 g of a mixture consisting of the target compound (I-52) and its isomer(s) were obtained. Physical properties and elemental analysis data of the compound so obtained are shown below:

Visible absorption:
$\lambda_{max} = 705$ nm
$\epsilon g = 2.5 \times 10^5$ ml/g·cm
(Solvent: toluene)

| Elemental analysis: $C_{88}H_{132}N_{12}S_{16}Zn$ | | | |
|---|---|---|---|
| | C | H | N |
| Calculated (%) | 54.62 | 6.83 | 8.69 |
| Found (%) | 54.60 | 6.85 | 8.70 |

In a vessel equipped with a stirrer and a nitrogen inlet tube, 36.8 g of 4,4'-bis(2-aminophenoxy)biphenyl and 202 g of N,N-dimethylformamide were charged. 4,4'-(p-Phenylenedioxy)diphthalic dianhydride (39.8 g) were added in portions at room temperature in a nitrogen atmosphere, followed by stirring for 20 hours. To the resultant polyamidic acid solution, 3.0 g of the compound (I-52) were added and mixed. The mixture was thereafter cast on a glass substrate, followed by heat treatment at 200° C. for 5 hours. The filter so obtained was found to have not only good transmittance characteristics but also excellent durability.

In addition, a solution of the phthalocyanine compound (I-52) in n-octane (10 g/l) was coated on a polycarbonate substrate, whereby an optical recording medium with gold as a reflective layer was fabricated. That optical recording medium showed 70% reflectance at 780–830 nm, and 59 dB sensitivity as measured on the basis of reflection of a 780 nm laser beam of 7 mW from its substrate at 1800 rpm.

EXAMPLE 53

In a vessel equipped with a stirrer, a reflux condenser and a nitrogen inlet tube, 10 g of 6-bromo-3-nitrophthalonitrile, 70 g of dried dimethylformamide (DMF) and 30 g of dried toluene were charged. They were thereafter converted completely into a solution, followed by cooling to 0° C. To the resulting solution, 100 g of a solution of 16.4 g of sodium sulfide (the compound represented by the below-described formula VII-12), which had been prepared from sodium hydride, in DMF/toluene (7/3) was added dropwise at 0° to −5° C. After the temperature was raised to room temperature, the resulting solution was stirred for 2 hours. The target compound was obtained from the thus-obtained reaction mixture by extracting it with toluene and then purified by column chromatography, whereby 13 g of phthalonitrile (the compound represented by the below-described formula V-43) were obtained.

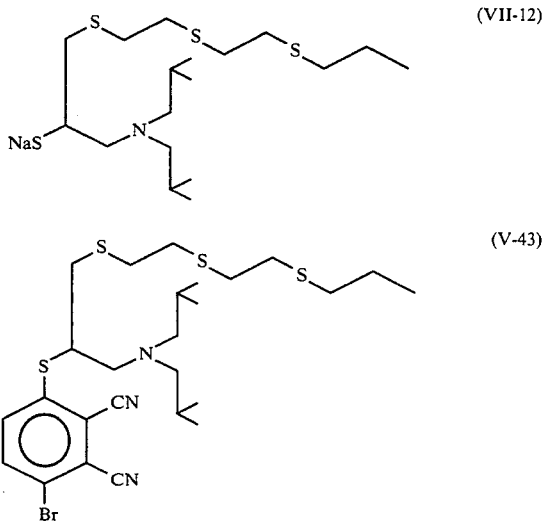

In a vessel equipped with a stirrer, a reflux condenser and a nitrogen inlet tube, 10 g (16.6 mmol) of the above-obtained phthalonitrile (V-43), 2.5 g of 1,8-diazabicyclo[5.4.0]-7-undecene and 120 g of n-amyl alcohol were charged, followed by heating to 110° C. in a nitrogen atmosphere. At the same temperature, 1.35 g (6.1 mmol) of $InCl_3$ were added, followed by reaction at 110°–120° C. for 8 hours. After the completion of the reaction, the reaction mixture was cooled and insoluble matter was removed by filtration. The filtrate was concentrated under reduced pressure to distill off the solvent. The residue was purified by column chromatography, whereby 8.1 g of a mixture consisting of the target compound (I-53) and its isomer(s) were obtained. Physical properties and elemental analysis data of the compound so obtained are shown below:

Visible absorption:
$\lambda_{max}$=715 nm
$\epsilon g = 2.2 \times 10^5$ ml/g·cm
(Solvent: toluene)

| Elemental analysis: $C_{104}H_{160}N_{12}S_{16}ClBr_4In$ | | | |
|---|---|---|---|
| | C | H | N |
| Calculated (%) | 48.79 | 6.26 | 6.57 |
| Found (%) | 48.81 | 6.30 | 6.60 |

One gram of the phthalocyanine compound (I-53) was added to 100 g of polystyrene. The resulting resin composition was injection-molded, whereby a filter was fabricated. The filter so obtained was found to have not only good transmittance characteristics but also have excellent durability.

In addition, a solution (10 g/l) of the phthalocyanine compound (I-53) in n-octane was coated on a polycarbonate substrate, whereby an optical recording medium with gold as a reflective layer was fabricated. That optical recording medium showed 73% reflectance at 780–830 nm, and 60 dB sensitivity as measured on the basis of reflection of a 780 nm laser beam of 7 mW from its substrate at 1800 rpm.

EXAMPLE 54

In a vessel equipped with a stirrer, a reflux condenser and a nitrogen inlet tube, 10 g of 4,6-diiodo-3-nitrophthalonitrile, 70 g of dried dimethylformamide (DMF) and 30 g of dried toluene were charged. They were thereafter converted completely into a solution, followed by cooling to 0° C. To the resulting solution, 100 g of a solution of 9.5 g of sodium sulfide (the compound represented by the below-described formula VII-13), which had been prepared from sodium hydride, in DMF/toluene (7/3) was added dropwise at 0° to −5° C. After the temperature was raised to room temperature, the resulting solution was stirred for 2 hours. The target compound was obtained from the thus-obtained reaction mixture by extracting it with toluene and then purified by column chromatography, whereby 13 g of phthalonitrile (the compound represented by the below-described formula V-44) were obtained.

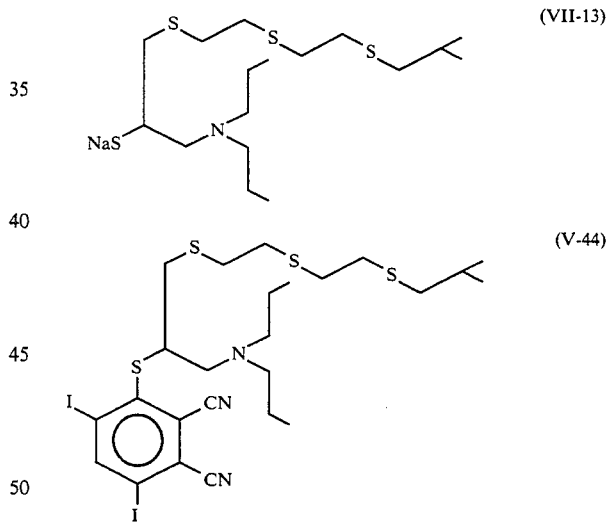

In a vessel equipped with a stirrer, a reflux condenser and a nitrogen inlet tube, 12 g (16.4 mmol) of the above-obtained phthalonitrile (V-44), 2.5 g of 1,8-diazabicyclo[5.4.0]-7-undecene and 120 g of n-amyl alcohol were charged, followed by heating to 110° C. in a nitrogen atmosphere. At the same temperature, 0.6 g (4.7 mmol) of $MnCl_2$ was added, followed by reaction at 110°–120° C. for 8 hours. After the completion of the reaction, the reaction mixture was cooled and insoluble matter was removed by filtration. The filtrate was concentrated under reduced pressure to distill off the solvent. The residue was purified by column chromatography, whereby 10.1 g of a mixture consisting of the target compound (I-54) and its isomer(s) were obtained. Physical properties and elemental analysis data of the compound so obtained are shown below:

Visible absorption:
$\lambda_{max} = 716$ nm
$\epsilon g = 2.3 \times 10^5$ ml/g·cm
(Solvent: toluene)

Elemental analysis: $C_{100}H_{148}N_{12}S_{16}I_8Mn$

|  | C | H | N |
|---|---|---|---|
| Calculated (%) | 38.73 | 4.78 | 5.42 |
| Found (%) | 38.72 | 4.79 | 5.43 |

One gram of the phthalocyanine compound (I-54) was added to 100 g of polystyrene. The resulting resin composition was injection-molded, whereby a filter was fabricated. The filter so obtained was found to have not only good transmittance characteristics but also have excellent durability.

In addition, a solution (10 g/l) of the phthalocyanine compound (I-54) in n-octane was coated on a polycarbonate substrate, whereby an optical recording medium with gold as a reflective layer was fabricated. That optical recording medium showed 72% reflectance at 780-830 nm, and 61 dB sensitivity as measured on the basis of reflection of a 780 nm laser beam of 7 mW from its substrate at 1800 rpm.

EXAMPLE 55

In a vessel equipped with a stirrer, a reflux condenser and a nitrogen inlet tube, 10 g of 4,5-dichloro-3,6-dinitrophthalonitrile, 70 g of dried dimethylformamide (DMF) and 30 g of dried toluene were charged. They were thereafter converted completely into a solution, followed by cooling to 0° C. To the resulting solution, 100 g of a solution of 20.3 g of sodium sulfide (the compound represented by the below-described formula VII-14), which had been prepared from sodium hydride, in DMF/toluene (7/3) was added dropwise at 0° to −5° C. After the temperature was raised to room temperature, the resulting solution was stirred for 2 hours. The target compound was obtained from the thus-obtained reaction mixture by extracting it with toluene and then purified by column chromatography, whereby 24 g of phthalonitrile (the compound represented by the below-described formula V-45) were obtained.

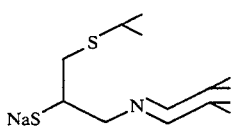

(VII-14)

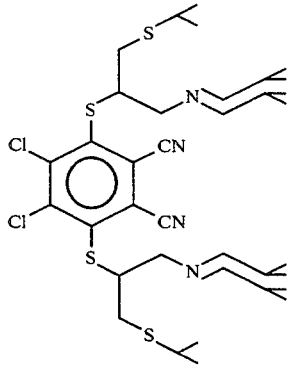

(V-45)

In a vessel equipped with a stirrer, a reflux condenser and a nitrogen inlet tube, 20 g (26.8 mmol) of the above-obtained phthalonitrile (V-45), 4.1 g of 1,8-diazabicyclo[5.4.0]-7-undecene and 100 g of n-amyl alcohol were charged, followed by heating to 110° C. in a nitrogen atmosphere. At the same temperature, 1.15 g (11.6 mmol) of CuCl were added, followed by reaction at 110°–120° C. for 8 hours. After the completion of the reaction, the reaction mixture was cooled and insoluble matter was removed by filtration. The filtrate was concentrated under reduced pressure to distill off the solvent. The residue was purified by column chromatography, whereby 13 g of a mixture consisting of the target compound (I-55) and its isomer(s) were obtained. Physical properties and elemental analysis data of the compound so obtained are shown below:

Elemental analysis: $C_{144}H_{240}N_{16}S_{16}Cl_8Cu$

|  | C | H | N |
|---|---|---|---|
| Calculated (%) | 56.63 | 7.87 | 7.34 |
| Found (%) | 56.62 | 7.89 | 7.34 |

Mixed into a homogeneous solution were 122 g of 1,4-bis($\alpha,\alpha$-dimethylisocyanatomethyl)benzene, 117 g of 1,3,5-tris(3-mercaptopropyl)isocyanurate, 10 g of the compound (I-55) and 0.3 g of dibutyltin dilaurate. The solution was poured into a mold formed of glasses, which had been subjected to surface treatment with a fluorine-base external mold releasing agent, with PVC gasket.

After heated at 70° C. for 4 hours, at 80° C. for 2 hours, at 90° C. for 2 hours, at 100° C. for 2 hours and at 120° C. for 2 hours, the mold was cooled and the filter so molded was released. The filter exhibited good transmittance characteristics and were also excellent in light resistance and moisture resistance.

In addition, a solution (10 g/l) of the phthalocyanine compound (I-55) in n-octane was coated on a polycarbonate substrate, whereby an optical recording medium with gold as a reflective layer was fabricated. That optical recording medium showed 69% reflectance at 780-830 nm, and 62 dB sensitivity as measured on the basis of reflection of a 780 nm laser beam of 7 mW from its substrate at 1800 rpm.

EXAMPLE 56

In a vessel equipped with a stirrer, a reflux condenser and a nitrogen inlet tube, 10 g of 6-chloro-3-nitrophthalonitrile, 70 g of dried dimethylformamide (DMF) and 30 g of dried toluene were charged. They were thereafter converted completely into a solution, followed by cooling to 0° C. To the resulting solution, 100 g of a solution of 18.6 g of sodium sulfide (the compound represented by the below-described formula VII-15), which had been prepared from sodium hydride, in DMF/toluene (7/3) was added dropwise at 0° to −5° C. After the temperature was raised to room temperature, the resulting solution was stirred for 2 hours. The target compound was obtained from the thus-obtained reaction mixture by extracting it with toluene and then purified by column chromatography, whereby 19 g of phthalonitrile (the compound represented by the below-described formula V-46) were obtained.

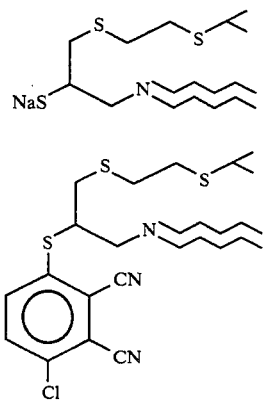
(VII-15)

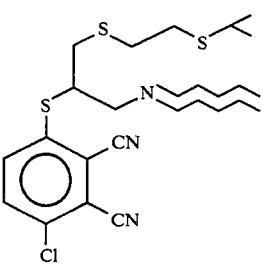
(V-46)

In a vessel equipped with a stirrer, a reflux condenser and a nitrogen inlet tube, 15 g (28.6 mmol) of the above-obtained phthalonitrile (V-46), 4.3 g of 1,8-diazabicyclo[5.4.0]-7-undecene and 110 g of n-amyl alcohol were charged, followed by heating to 110° C. in a nitrogen atmosphere. At the same temperature, 0.85 g (8.6 mmol) of CuCl was added, followed by reaction at 110°–120° C. for 8 hours. After the completion of the reaction, the reaction mixture was cooled and insoluble matter was removed by filtration. The filtrate was concentrated under reduced pressure to distill off the solvent. The residue was purified by column chromatography, whereby 10.5 g of a mixture consisting of the target compound (I-56) and its isomer(s) were obtained. Physical properties and elemental analysis data of the compound so obtained are shown below:

Visible absorption:
$\lambda_{max}$=712 nm
$\epsilon g$=2.2×10$^5$ ml/g·cm
(Solvent: toluene)

| Elemental analysis: $C_{104}H_{160}N_{12}S_{12}Cl_4Cu$ | | | |
|---|---|---|---|
| | C | H | N |
| Calculated (%) | 57.63 | 7.39 | 7.76 |
| Found (%) | 57.62 | 7.40 | 7.77 |

One gram of the phthalocyanine compound (I-56) was added to 100 g of polystyrene. The resulting resin composition was injection-molded, whereby a filter was fabricated. The filter so obtained was found to have not only good transmittance characteristics but also excellent durability.

A solution (10 g/l) of the phthalocyanine compound (I-56) in n-octane was coated on a polycarbonate substrate, whereby an optical recording medium with gold as a reflective layer was fabricated. That optical recording medium showed 70% reflectance at 780-830 nm, and 60 dB sensitivity as measured on the basis of reflection of a 780 nm laser beam of 7 mW from its substrate at 1800 rpm.

EXAMPLE 57

In a vessel equipped with a stirrer, a reflux condenser and a nitrogen inlet tube, 10 g of 3-nitrophthalonitrile, 70 g of dried dimethylformamide (DMF) and 30 g of dried toluene were charged. They were thereafter converted completely into a solution, followed by cooling to 0° C. To the resulting solution, 100 g of a solution of 23.5 g of sodium sulfide (the compound represented by the below-described formula VII-16), which had been prepared from sodium hydride, in DMF/toluene (7/3) was added dropwise at 0° to −5° C. After the temperature was raised to room temperature, the resulting solution was stirred for 2 hours. The target compound was obtained from the thus-obtained reaction mixture by extracting it with toluene and then purified by column chromatography, whereby 21 g of phthalonitrile (the compound represented by the below-described formula V-47) were obtained.

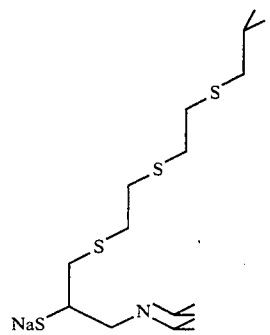
(VII-16)

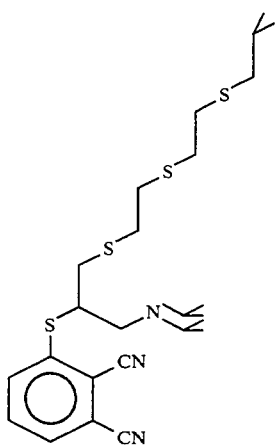
(V-47)

In a vessel equipped with a stirrer, a reflux condenser and an ammonia gas inlet tube, 20 g of the above-obtained phthalonitrile (V-47), 200 g of methanol and 1.1 g of sodium methylate were charged, followed by the blowing of ammonia gas at a molar ratio of 6.4 times relative to the compound V-47. After the contents were heated to 55°–60° C., they were reacted under heating for 2 hours. Methanol was thereafter distilled off under reduced pressure and organic substance was extracted with toluene. Hexane was added and crystals were precipitated, whereby 18 g of the target compound (VI-12) were obtained.

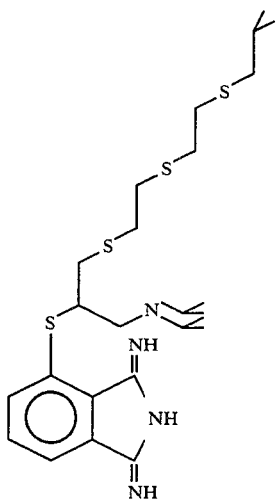

(VI-12)

A mixture consisting of 1.01 g of CuCl and 300 g of quinoline was heated to 200° C. To the mixture, 18 g of the above-obtained diiminoisoindoline derivative (VI-12) were added, followed by heating under reflux for 5 hours. The reaction mixture was poured into 1000 g of methanol. After suction filtration, crystals so collected were washed with methanol, followed by drying, whereby 16 g of a mixture consisting of the compound (I-57) and its isomer(s) were obtained. Physical properties and elemental analysis data of the compound so obtained are shown below.

Visible absorption:
$\lambda_{max} = 709$ nm
$\epsilon g = 2.4 \times 10^5$ ml/g·cm
(Solvent: toluene)

| Elemental analysis: $C_{100}H_{156}N_{12}S_{16}Cu$ | | | |
|---|---|---|---|
| | C | H | N |
| Calculated (%) | 57.16 | 7.43 | 8.00 |
| Found (%) | 57.14 | 7.53 | 8.03 |

One gram of the phthalocyanine compound (I-57) was added to 100 g of polystyrene. The resulting resin composition was injection-molded, whereby a filter was fabricated. The filter so obtained was found to have not only good transmittance characteristics but also excellent durability.

One gram of the phthalocyanine compound (I-57) was dissolved in 100 g of dibutyl ether and the resulting solution was coated on a polycarbonate substrate for optical disc. The optical disc thus fabricated was found to have a reflectance of 36% and a sensitivity of 51 dB in terms of C/N ratio as measured at a linear velocity of 5.5 m/sec by a 780 nm laser beam of 8 mW.

A solution (10 g/l) of the phthalocyanine compound (I-57) in n-octane was coated on a polycarbonate substrate, whereby an optical recording medium with gold as a reflective layer was fabricated. That optical recording medium showed 70% reflectance at 780–830 nm, and 57 dB sensitivity as measured on the basis of reflection of a 780 nm laser beam of 7 mW from its sub-strate at 1800 rpm.

EXAMPLE 58-124

In each example, one to four of the phthalonitriles represented by the below-described formula (V) (Table 7) or of the diiminoisoindolines represented by the below-described formula (VI) (Table 8) were reacted with a metal derivative under the conditions shown in Table 9, whereby a phthalocyanine compound and its isomer(s) were both synthesized. A filter fabricated using the thus-obtained compound was found to be excellent in transmittance characteristics and durability. In addition, an optical recording medium fabricated using the respective compound of from I-58 to I-78 was found to have good reflectance, sensitivity and durability.

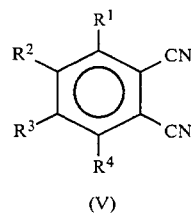

(V)

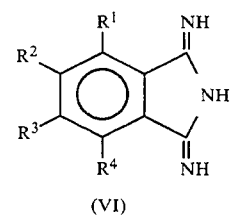

(VI)

TABLE 7

| Intermediate | R¹ | R² | R³ | R⁴ |
|---|---|---|---|---|
| V-48 | [structure: -S-CH₂CH₂-N=CH-CH=CH₂] | [structure: -S-C₆H₄-Cl (para)] | [structure: -S-C₆H₄-Cl (para)] | H |
| V-49 | [structure: -S-CH₂CH₂CH₂-N=CH-CH(CH₃)₂] | COO—CH₃ | H | H |
| V-50 | [structure: -S-CH₂CH₂-S-CH₂CH₂-N=CH-CH(CH₃)₂] | N(CH₃)₂ | N(CH₃)₂ | H |
| V-51 | [structure: -S-CH₂CH₂-S-CH₂CH₂-N=CH-CH(CH₃)₂] | SH | SH | H |
| V-52 | [structure: -S-CH₂CH₂CH₂-S-CH₂CH₂CH₂-N=CH-CH=CH₂] | H | I | I |
| V-53 | [structure: -S-CH₂CH(CH₃)-N(CH(CH₃)₂)₂] | [structure: 3-chloro-methoxyphenyl] | [structure: 3-chloro-methoxyphenyl] | H |
| V-54 | [structure: -S-CH₂CH(CH₃)-N(CH₂CH₂CH₃)₂] | H | H | [structure: -S-CH₂CH(CH₃)-N(CH₂CH₂CH₃)₂] |
| V-55 | [structure: -S-CH₂CH₂-N=CH-CH=CH₂] | Cl | H | Cl |
| V-56 | [structure: -S-CH₂CH₂-N=CH-CH(CH₃)₂] | Cl | H | [structure: -S-CH₂CH₂-N=CH-CH(CH₃)₂] |
| V-57 | [structure: -S-CH₂-N=CH-CH(CH₃)₂] | I | H | [structure: -S-CH₂-N=CH-CH(CH₃)₂] |

TABLE 7-continued

| Intermediate | R¹ | R² | R³ | R⁴ |
|---|---|---|---|---|
| V-58 | CH₃CH₂-O-CH₂CH₂-O-CH₂CH₂-O-CH₂CH₂-O— | H | H | H |
| V-59 | CH₃CH₂CH₂-O-CH₂CH₂-O— | H | H | Br |
| V-60 | (CH₃)₂CH-O-CH₂CH₂-O— | H | H | Cl |
| V-61 | (CH₃)₂CHCH₂-O-CH₂CH₂-O— | H | H | CH₃ |
| V-62 | (CH₃)₂CHCH₂-O-CH₂CH(CH₃)-O— | H | Cl | (CH₃)₂CHCH₂-O-CH₂-O— |
| V-63 | (CH₃)₂CHCH₂-O-CH₂CH₂-O-CH₂CH₂-O-CH₂CH₂-O— | H | I | (CH₃)₂CHCH₂-O-CH₂CH₂-O-CH₂CH₂-O-CH₂CH₂-O— |
| V-64 | (CH₃)₂CHCH₂-O-CH₂CH(CH₃)-O-CH₂CH(CH₃)-O— | SPh | SPh | H |
| V-65 | CH₃CH₂CH₂CH₂-O-CH₂CH(CH₃)-O-CH₂CH(CH₃)-O— | H | H | CH₃CH₂CH₂CH₂-O-CH₂CH(CH₃)-O-CH₂CH(CH₃)-O— |
| V-66 | (CF₃)₃C-CF₂-CH₂-O— | Cl | Cl | Cl |

TABLE 7-continued

| Intermediate | R¹ | R² | R³ | R⁴ |
|---|---|---|---|---|
| V-67 | —CH₂OCH₂CH₂CH(CH₃)₂ | H | H | —CH₂OCH₂CH₂CH(CH₃)₂ |
| V-68 | —OCH(CH₃)CH₂CH₃ | —OC₆H₅ | —OC₆H₅ | —OCH(CH₃)CH₂CH₃ |
| V-69 | —OCH(CH₃)CH(CH₃)₂ | 4-Cl-C₆H₄-S— | 4-Cl-C₆H₄-S— | —OCH(CH₃)CH(CH₃)₂ |
| V-70 | —OCH₂CH(CH₃)CH₂CH(CH₃)₂ | H | Cl | Cl |
| V-71 | —OCH₂CH₂CH(CH₃)₂ | H | I | I |
| V-72 | —OCH₂CH₂OH | NH(CH₃) | NH(CH₃) | —OCH₂CH₂OH |
| V-73 | —OCH₂CH(CH₂OH)CH₂CH₃ | H | Cl | —OCH₂CH(CH₂OH)OCH₃ |
| V-74 | —OCH(OH)CH₂CH₂CH₃ | N(CH₃)₂ | N(CH₃)₂ | H |
| V-75 | —S(CH₂CH₂S)₃CH₂CH₃ | 4-Cl-C₆H₄-S— | 4-Cl-C₆H₄-S— | H |
| V-76 | —SCH₂CH₂SCH₂CH₃ | H | H | H |
| V-77 | —SCH₂CH(CH₃)SCH₂CH₃ | H | H | Br |
| V-78 | —SCH₂CH₂CH(CH₃)SCH₂CH₃ | H | H | Cl |

TABLE 7-continued
| Intermediate | R¹ | R² | R³ | R⁴ |
|---|---|---|---|---|
| V-79 |  | H | H |  |
| V-80 |  | H | Cl | Cl |
| V-81 |  | COOC₂H₅ | H | H |
| V-82 |  | OH | H | Cl |
| V-83 |  | H | H | H |
| V-84 |  | H | Cl | Cl |
| V-85 |  | H | H |  |
| V-86 |  | H | H | H |
| V-87 | | H | Br | H |
| V-88 | | H | H | Br |

TABLE 7-continued

| Intermediate | R¹ | R² | R³ | R⁴ |
|---|---|---|---|---|
| V-89 | -S-CH₂CH₂-SH | H | H | H |
| V-90 | -S-CH(CH₃)CH₂CH₂-SH | H | H | -S-CH(CH₃)CH₂CH₂-SH |
| V-91 | -S-CH₂CH(CH₃)CH₂-SH | H | Cl | Cl |
| V-92 | n-hexyl | H | H | H |
| V-93 | isobutyl | H | H | isobutyl |
| V-94 | -CH₂CH₂CH₂Cl | H | Br | Br |
| V-95 | -CH₂CH₂CH₂CH₂Br | H | H | Br |
| V-96 | long alkyl chain | H | H | H |
| V-97 | -(CH₂)ₙ-OH | H | H | Br |
| V-98 | perfluoroalkyl (C(CF₃)₂CF₂CF₃ type) | H | H | H |
| V-99 | -(CH₂)₅-SH | H | H | Cl |
| V-100 | -CH₂CH(OCH₃)CH₂N(CH₃)₂ | OCH₃ | H | H |
| V-101 | -CH₂CH(OCH₃)CH₂N=CH₂ | OCH₃ | OCH₃ | H |

TABLE 7-continued

| Intermediate | R¹ | R² | R³ | R⁴ |
|---|---|---|---|---|
| V-102 | ![structure: CH2=CH-CH2-N(-)-CH2-CH(OCH3)-O-] | OCH₃ | H | H |
| V-103 | H | H | OC₂H₅ | ![structure: CH2=CH-CH2-N(OCH3)-CH2-CH(OCH3)-O-] |

TABLE 8

| Intermediate | R¹ | R² | R³ | R⁴ |
|---|---|---|---|---|
| VI-13 | —S-CH(CH₂SCH₂CH(CH₃)₂)CH₂N=CH-CH=CH₂ | SPh | SPh | H |
| VI-14 | —S-CH(CH₂SCH₂CH₂SC₂H₅)CH(C₂H₅)N=CH-CH=CH₂ | SPh | SPh | Cl |
| VI-15 | —S-CH(C₄H₉)CH₂N=CH-CH=CH-CH₃ | H | Br | Br |
| VI-16 | —S-CH(C₄H₉)CH₂N=CH-CH=CH-CH=CH₂ | S—CH₃ | S—CH₃ | H |
| VI-17 | —S-CH(CH₂N=CH-CH=CH₂)CH₂N=CH-CH=CH₂ | H | CH₃ | Br |
| VI-18 | —S-CH(CH₂N(iBu)CH₂...N(iBu)...) (bicyclic diamine with isobutyl groups) | H | C₂H₅ | H |
| VI-19 | —S-CH(CH₂CH(CH₃)₂)CH₂N(iBu)₂ | NHC₂H₅ | NHC₂H₅ | H |
| VI-20 | —S-CH₂CH₂-S-CH₂CH₂-S-CH₂CH₂-S-CH₂CH₂-N(CH₃)₂ | OPh | OPh | H |
| VI-21 | —S-CH₂CH₂-S-CH₂CH₂-S-CH₂CH₂-N=CH-CH=CH₂ | —O-C₆H₄-Cl | —O-C₆H₄-Cl | Cl |
| VI-22 | —S-CH(CH₂SCH₂CH₂SC₂H₅)CH₂N(CH₃)₂ | H | H | H |

TABLE 8-continued

| Intermediate | R¹ | R² | R³ | R⁴ |
|---|---|---|---|---|
| VI-23 | —S-CH₂CH₂-S-CH₂CH₂-S-CH₂CH₂-N(isobutyl)₂ (structure) | H | H | Cl |

TABLE 9

| Cmp'd | Metal | Preparation process | $\lambda_{max}$ |
|---|---|---|---|
| I-58 | Cu | Reaction of CuCl and the intermediate (VI-13) in quinoline | 761 |
| I-59 | Pd | Reaction of PdCl2 and the intermediate (VI-14) in quinoline | 758 |
| I-60 | Co | Reaction Of COCl₂ and the intermediate (VI-15) in quinoline | 710 |
| I-61 | Zn | Reaction of Zn(OAc)₂ and the intermediate (V-16) in quinoline | 735 |
| I-62 | Fe | Reaction of FeCl₂ and the intermediate (VI-17) in quinoline | 708 |
| I-63 | Fe | Reaction of FeCl₂ and the intermediate (VI-18) in quinoline | 705 |
| I-64 | VO | Reaction of VO(acac)₂ and the intermediate (V-19) in quinoline | 740 |
| I-65 | SiCl₂ | Reaction of SiCl4 and the intermediate (VI-20) in quinoline | 725 |
| I-66 | Si(OH)₂ | Hydrolysis with ammonia after reaction Of SiCl₄ and the intermediate (VI-21) in quinoline | 719 |
| I-67 | Cu | Reaction of CuCl and the intermediate (VI-22) in quinoline | 705 |
| I-68 | VO | Reaction of VO(acac)₂ and the intermediate (VI-23) in quinoline | 725 |
| I-69 | Cu | Reaction of CuCl, the intermediate (V-48) and DBU in amyl alcohol | 760 |
| I-70 | Cu | Reaction of CuCl, the intermediate (V-49) and DBU in amyl alcohol | 720 |
| I-71 | Co | Reaction of CoCl₂, the intermediate (V-50) and DBU in amyl alcohol | 735 |
| I-72 | Co | Reaction Of CoCl₂, the intermediate (V-51) and DBU in amyl alcohol | 749 |
| I-73 | Mn | Reaction of MnCl₂, the intermediate (V-52) and DBU in amyl alcohol | 723 |
| I-74 | Fe | Reaction of FeCl₂, the intermediate (V-53) and DBU in chloronaphthalene | 730 |
| I-75 | Cu | Reaction of CuCl, the intermediate (V-54) and DBU in chloronaphthalene | 750 |
| I-76 | Cu | Reaction of CuCl, the intermediate (V-55) and DBU in chloronaphthalene | 716 |
| I-77 | Cu | Reaction of CuCl, the intermediate (V-56) and DBU in chloronaphthalene | 755 |
| I-78 | Fe | Reaction of FeCl₂, the intermediate (V-57) and DBU in chloronaphthalene | 758 |
| I-79 | Zn | Reaction of Zn(OAc)₂, the intermediate (V-58) and DBU in chloronaphthalene | 700 |
| I-80 | VO | Reaction of VO(acac)₂, the intermediate (V-59) and DBU in chloronaphthalene | 729 |
| I-81 | VO | Reaction of VO(acac)₂, the intermediate (V-60) and DBU in chloronaphthalene | 728 |
| I-82 | VO | Reaction of VO(acac)₂, the intermediate (V-61) and DBU in amyl alcohol | 720 |
| I-83 | Pd | Reaction of PdCl₂, the intermediate (V-62) and DBU in amyl alcohol | 745 |
| I-84 | Fe | Reaction of FeCl₂, the intermediate (V-63) and DBU in amyl alcohol | 755 |
| I-85 | Cu | Reaction of CuCl, the intermediate (V-64) and DBU in amyl alcohol | 765 |
| I-86 | Cu | Reaction of CuCl, the intermediate (V-65) and DBU in amyl alcohol | 745 |
| I-87 | Cu | Reaction of CuCl, the intermediate (V-66) and DBU in chloronaphthalene | 695 |
| I-88 | Fe | Reaction of FeCl₂, the intermediate (V-67) and DBU in amyl alcohol | 750 |
| I-89 | Fe | Reaction of FeCl₂, the intermediate (V-68) and DBU in amyl alcohol | 777 |
| I-90 | Co | Reaction Of CoCl₂, the intermediate (V-69) and DBU in amyl alcohol | 790 |
| I-91 | Pd | Reaction of PdCl₂, the intermediate (V-70) and DBU in amyl alcohol | 703 |
| I-92 | Ni | Reaction of NiCl₂, the intermediate (V-71) and DBU in amyl alcohol | 705 |
| I-93 | GeCl₂ | Reaction of GeCl₄, the intermediate (V-72) and DBU in amyl alcohol | 750 |
| I-94 | Zn | Reaction of Zn(OAc)₂, the intermediate (V-73) and DBU in amyl alcohol | 758 |
| I-95 | Zn | Reaction of Zn(OAc)₂, the intermediate (V-74) and DBU in amyl alcohol | 735 |
| I-96 | Pb | Reaction of Pb(OAc)₂, the intermediate (V-75) and DBU in amyl alcohol | 765 |
| I-97 | Zn | Reaction of Zn(OAc)₂, the intermediate (V-76) and DBU in amyl alcohol | 715 |
| I-98 | Cu | Reaction of CuCl, the intermediate (V-77) and DBU in amyl alcohol | 716 |
| I-99 | Ni | Reaction of NiCl₂, the intermediate (V-78) and DBU in amyl alcohol | 716 |
| I-100 | Ni | Reaction of NiCl₂, the intermediate (V-79) and DBU in amyl alcohol | 751 |
| I-101 | Fe | Reaction of FeCl₂, the intermediate (V-80) and DBU in amyl alcohol | 725 |
| I-102 | Cu | Reaction of CuCl, the intermediate (V-81) and DBU in amyl alcohol | 724 |
| I-103 | Zn | Reaction of Zn(OAc)₂, the intermediate (V-82) and DBU in amyl alcohol | 715 |
| I-104 | Pd | Reaction of PdCl₂, the | 708 |

TABLE 9-continued

| Cmp'd | Metal | Preparation process | $\lambda_{max}$ |
|---|---|---|---|
| I-105 | Pd | Reaction of PdCl$_2$, the intermediate (V-83) and DBU in chloronaphthalene | 713 |
| I-106 | Zn | Reaction of Zn(OAc)$_2$, the intermediate (V-84) and DBU in chloronaphthalene | 750 |
| I-107 | SiCl$_2$ | Reaction Of SiCl$_4$, the intermediate (V-85) and DBU in chloronaphthalene | 715 |
| I-108 | Fe | Reaction of FeCl$_2$, the intermediate (V-86) and DBU in chloronaphthalene | 717 |
| I-109 | Co | Reaction of CoCl$_2$, the intermediate (V-87) and DBU in chloronap4thalene | 719 |
| I-110 | Cu | Reaction of CuCl, the intermediate (V-88) and DBU in chloronaphthalene | 715 |
| I-111 | Pd | Reaction of PdCl$_2$, the intermediate (V-89) and DBU in chloronaphthalene | 752 |
| I-112 | Pb | Reaction of Pb(OAc)$_2$, the intermediate (V-90) and DBU in chloronaphthalene | 725 |
| I-113 | Cu | Reaction of CuCl, the intermediate (V-91) and DBU in chloronaphthalene | 685 |
| I-114 | Cu | Reaction of CuCl, the intermediate (V-92) and DBU in chloronaphthalene | 686 |
| I-115 | Fe | Reaction of FeCl$_2$, the intermediate (V-93) and DBU in chloronaphthalene | 694 |
| I-116 | Fe | Reaction of FeCl$_2$, the intermediate (V-94) and DBU in chloronaphthalene | 692 |
| I-117 | Fe | Reaction of FeCl$_2$, the intermediate (V-95) and DBU in amyl alcohol | 682 |
| I-118 | Cu | Reaction of CuCl, the intermediate (V-96) and DBU in amyl alcohol | 686 |
| I-119 | Cu | Reaction of CuCl, the intermediate (V-97) and DBU in amyl alcohol | 679 |
| I-120 | Co | Reaction of CoCl$_2$, the intermediate (V-98) and DBU in chloronaphthalene | 689 |
| I-121 | Cu | Reaction of CuCl, the intermediate (V-99) and DBU in amyl alcohol | 705 |
| I-122 | Co | Reaction Of CoCl$_2$, the intermediate (V-100) and DBU in amyl alcohol | 715 |
| I-123 | Cu | Reaction of CuCl, the intermediate (V-101) and DBU in amyl alcohol | 785 |
| I-124 | Pb | Reaction of Pb(OAc)$_2$, the intermediate (V-102) and DBU in amyl alcohol | 718 |

What is claimed is:

1. A color filter comprising a layer having good light transmittance which contains a phthalocyanine compound represented by the formula (I):

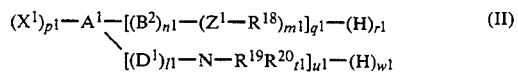

wherein $R^1$, $R^4$, $R^5$, $R^8$, $R^9$, $R^{12}$, $R^{13}$ and $R^{16}$ each independently represent a group represented by the formula (II) below or a hydrogen or a halogen atom, with the proviso that in each of the combinations of $R^1$ and $R^4$, $R^5$ and $R^8$, $R^9$ and $R^{12}$, and $R^{13}$ and $R^{16}$ groups, at least one of the groups is represented by formula (II) below; $R^2$, $R^5$, $R^6$, $R^7$, $R^{10}$, $R^{11}$, $R^{14}$ and $R^{15}$ each independently represent an unsubstituted $C_{1-20}$ alkyl group, a $C_{1-20}$ alkyl group substituted by an alkyl group, an alkoxyl group, a halogen atom or an hydroxyl group, an unsubstituted $C_{1-20}$ alkoxy group, a $C_{1-20}$ alkoxyl group substituted by an alkyl group, an alkoxyl group, a halogen atom or an hydroxyl group, an unsubstituted $C_{1-20}$ alkylthio group, a $C_{1-20}$ alkylthio group substituted by an alkoxy group, a halogen atom or a mercapto group, an unsubstituted $C_{1-20}$ alkylamino group, a $C_{1-20}$ alkylamino group substituted by an alkoxyl group, a halogen atom or an hydroxyl group, an unsubstituted $C_{2-20}$ dialkylamino group, a $C_{2-20}$ dialkylamino group substituted by an alkoxyl group, a halogen atom or an hydroxyl group, an unsubstituted phenoxy group, a phenoxy group substituted by at least one member of the group consisting of $C_{1-5}$ alkyl groups, $C_{1-3}$ alkoxy groups and halogen atoms, an unsubstituted phenylthio group, a phenylthio group substituted by at least one member of the group consisting of $C_{1-5}$ alkyl groups, $C_{1-3}$ alkoxy groups and one or more halogen atoms, —COOR$^{17}$, $R^{17}$ being a hydrogen atom, an unsubstituted $C_{1-20}$ alkyl group, a $C_{1-20}$ alkyl group substituted by an alkoxy group, a halogen atom or a hydroxyl group, a hydroxyl or mercapto group or a halogen or hydrogen atom, subject to the proviso that all of $R^1$-$R^{16}$ cannot be alkoxy; and Met represents Zn, Mg, Si, Sn, Rh, Pt, Pd, Mo, Mn, Pb, Cu, Ni, Co, Fe, AlCl, InCl, FeCl, TiCl$_2$, SnCl$_2$, GeCl$_2$, TiO, VO or Si(OH)$_2$; Formula (II) being $$(X^1)_{p1}-A^1-[(B^2)_{n1}-(Z^1-R^{18})_{m1}]_{q1}-(H)_{r1} \atop {\diagdown \atop [(D^1)_{l1}-N-R^{19}R^{20}_{l1}]_{u1}-(H)_{w1}}} \quad (II)$$

wherein $X^1$ and $Z^1$ represent independently an oxygen or sulfur atom, $R^{18}$, $R^{19}$ and $R^{20}$ independently represent a hydrogen atom or an unsubstituted $C_{1-20}$ alkyl group or a $C_{1-20}$ alkyl group substituted by alkyl groups, alkoxy groups, halogen atoms or a hydroxyl group, $A^1$ represents a connecting group of the formula:

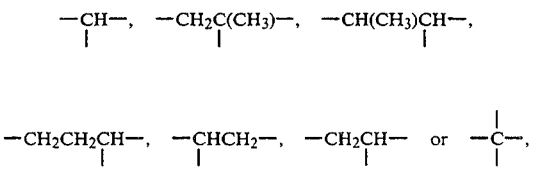

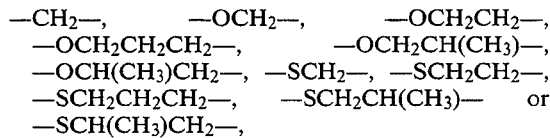

$B^1$ represents a connecting group of the formula:

—CH$_2$—, —OCH$_2$—, —OCH$_2$CH$_2$—, —OCH$_2$CH$_2$CH$_2$—, —OCH$_2$CH(CH$_3$)—, —OCH(CH$_3$)CH$_2$—, —SCH$_2$—, —SCH$_2$CH$_2$—, —SCH$_2$CH$_2$CH$_2$—, —SCH$_2$CH(CH$_3$)— or —SCH(CH$_3$)CH$_2$—, $D^1$ represents a connecting group of the formula:

—CH$_2$—, —OCH$_2$—, —OCH$_2$CH$_2$—, —OCH$_2$CH$_2$CH$_2$—, —OCH$_2$CH(CH$_3$)—, OCH(CH$_3$)CH$_2$—, —SCH$_2$—, —SCH$_2$CH$_2$, —SCH$_2$CH$_2$CH$_2$—, —SCH$_2$CH(CH$_3$)—, —SCH(CH$_3$)CH$_2$—, —CH(CH$_3$)—, —CH(CH$_3$)CH$_2$—, —CH(CH$_2$CH$_3$)— or —CH(CH$_2$CH$_2$CH$_3$)—, $n^1$ and $l^1$ each are an integer from 0 to 10, $m^1$, $q^1$, $t^1$, $u^1$, $r^1$ and $w^1$ each are an integer from 0 to 2, and $p^1$ is 0 or 1, with the proviso that, when $p^1$ and $m^1$ are 0, $t^1$ and $u^1$ each are other than 0 and $w^1$ is 0.

2. The color filter of claim 1, wherein in the formula (II), $q^1$ is 0, $r^1$ is 1, $t^1$ and $u^1$ are other than 0, and $w^1$ is 0.

3. The color filter of claim 1, wherein in the formula (II), $p^1$ is 1, $u^1$ is 0, $w^1$ is 1, and $q^1$ is other than 0.

4. The color filter of claim 1, wherein in the formula (II), $q^1$ is 0, $r^1$ is 1, $t^1$ is 1, $u^1$ is other than 0, and $w^1$ is 0.

5. The color filter of claim 1, wherein in the formula (II), $u^1$ is 0, $w^1$ is 1, $m^1$ is 1, $q^1$ is other than 0, and $r^1$ is 0.

6. The color filter of claim 1, wherein in the formula (II), $q^1$ is 0, $t^1$ is 1, $r^1$ is 1, $u^1$ is other than 0, $w^1$ is 0, $A^1$ is

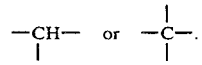

7. The color filter of claim 1, wherein in the formula (II), $u^1$ is 0, $w^1$ is 1, $m^1$ is 1, $q^1$ is other than 0, $r^1$ is 0, $A^1$ is

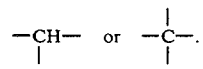

8. The color filter of claim 1, wherein in the formula (II), $u^1$ is 0, $w^1$, $q^1$ and $m^1$ are 1, $r^1$ is 0, $A^1$ is

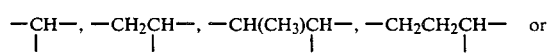

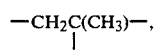

and $B^1$ is —U$^1$—(CH$_2$)$_y$—, —V$^1$—[CH(CH$_3$)CH$_2$]— or —W$^1$—[CH$_2$CH(CH$_3$)]— in which U$^1$, V$^1$ and W$^1$ independently represent an oxygen or sulfur atom and y is an integer of 1–3.

9. The color filter of claim 1, wherein in the formula (II), $q^1$ is 0, $t^1$, $u^1$ and $r^1$ are 1, $w^1$ is 0, $A^1$ is

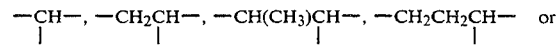

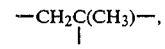

$D^1$ is —U$^2$—(CH$_2$)$_x$—, —V$^2$—[CH(CH$_3$)CH$_2$]— or —W$^2$—[CH$_2$CH(CH$_3$)]— in which U$^2$, V$^2$ and W$^2$ independently represent an oxygen or sulfur atom and x is an integer of 1–3.

10. The color filter of claim 1, wherein in formula (II), $q^1$, $u^1$, $m^1$ and $t^1$ are 1, $r^1$ and $w^1$ are 0, $A^1$ is

$B^1$ is —U$^3$—(CH$_2$)$_a$—, —V$^3$—[CH(CH$_3$)CH$_2$]— or W$^3$—[CH$_2$CH(CH$_3$)]—, in which U$^3$, V$^3$ and W$^3$ each independently represent an oxygen or sulfur atom, the subscript a being an integer of 1–3 and $D^1$ is —C(R$^{21}$)H—, $R^{21}$ represents a hydrogen atom or a methyl or ethyl group.

11. A phthalocyanine compound represented by the formula (III):

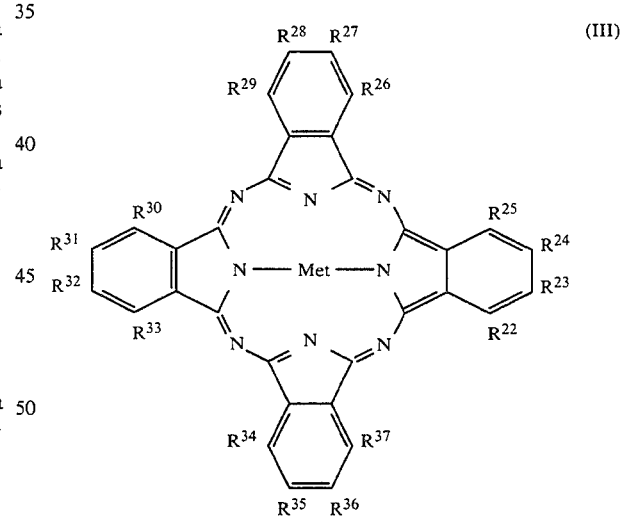

wherein $R^{22}$, $R^{25}$, $R^{26}$, $R^{29}$, $R^{30}$, $R^{33}$, $R^{34}$ and $R^{37}$ each independently is a group represented by formula (IV) or a hydrogen or halogen atom, with the proviso that, in each of the combinations of $R^{22}$ and $R^{25}$, $R^{26}$ and $R^{29}$, $R^{30}$ and $R^{33}$, and $R^{34}$ and $R^{37}$ groups, one of the groups is represented by formula (IV) and the other is a hydrogen or halogen atom; $R^{23}$, $R^{24}$, $R^{27}$, $R^{28}$, $R^{31}$, $R^{32}$, $R^{35}$ and $R^{36}$ each independently represent an unsubstituted C$_{1-10}$ alkyl group, a C$_{1-20}$ alkyl group substituted by an alkyl group, an alkoxyl group, a halogen atom or a hydroxyl group, an unsubstituted C$_{1-20}$ alkylamino group, a C$_{1-10}$ alkylamino group substituted by an alkoxy group, a halogen atom or a hydroxyl group, an unsubstituted $C_{2\text{-}20}$ dialkylamino group, a $C_{2\text{-}20}$ dialkylamino group substituted by an alkoxyl group, a halogen atom or a hydroxyl group, an unsubstituted phenoxy group, a phenoxy group substituted by at least one member of the group consisting of $C_{1\text{-}5}$ alkyl groups, $C_{1\text{-}3}$ alkoxy groups and halogen atoms, an unsubstituted phenylthio group, a phenylthio group substituted by at least one member of the group consisting of $C_{1\text{-}5}$ alkyl groups, $C_{1\text{-}3}$ alkoxyl groups and halogen atoms, —COOR$^{38}$ in which R$^{38}$ is a hydrogen atom, an unsubstituted $C_{1\text{-}20}$ alkyl group, a $C_{1\text{-}20}$ alkyl group substituted by an alkoxyl group, a halogen atom or a hydroxyl group, a hydroxy group, a mercapto group, a halogen atom or a hydrogen atom; and Met represents Zn, Mg, Si, Sn, Rh, Pt, Pd, Mo, Mn, Pb, Cu, Ni, Co, Fe, AlCl, InCl, FeCl, TiCl$_2$, SnCl$_2$, SiCl$_2$, GeCl$_2$, TiO, VO or Si(OH)$_2$; Formula (IV) being

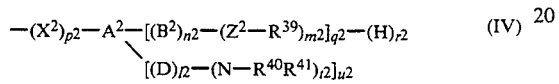

wherein $X^2$ and $Z^2$ each independently represent an oxygen or sulfur atom, R$^{39}$, R$^{40}$ and R$^{41}$ each independently represent a hydrogen atom, an unsubstituted $C_{1\text{-}20}$ alkyl group or a $C_{1\text{-}20}$ alkyl group substituted by an alkyl group, an alkoxy group, a halogen atom or a hydroxyl group, A$^2$ represents a connecting group represented by one of the following formulae:

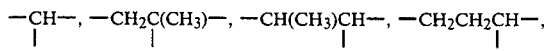

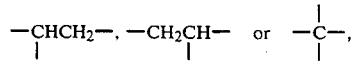

B$^1$ represents a connecting group of the formula:
—CH$_2$—, —OCH$_2$—, —OCH$_2$CH$_2$—, —OCH$_2$CH$_2$CH$_2$—, —OCH$_2$CH(CH$_3$)—, —OCH(CH$_3$)CH$_2$—, —SCH$_2$—, —SCH$_2$CH$_2$—, —SCH$_2$CH$_2$CH$_2$—, —SCH$_2$CH(CH$_3$)— or —SCH(CH$_3$)CH$_2$—, D$^1$ represents a connecting group of the formulae:
—CH$_2$—, —OCH$_2$—, —OCH$_2$CH$_2$—, —OCH$_2$CH$_2$CH$_2$—, —OCH$_2$CH(CH$_3$)—, OCH(CH$_3$)CH$_2$—, —SCH$_2$—, —SCH$_2$CH$_2$, —SCH$_2$CH$_2$CH$_2$—, —SCH$_2$CH(CH$_3$)—, —SCH(CH$_3$)CH$_2$—, —CH(CH$_3$)—, —CH(CH$_3$)CH$_2$—, —CH(CH$_2$CH$_3$)— or —CH(CH$_2$CH$_2$CH$_3$)—, wherein n$^1$ and l$^1$ each represent an integer from 0 to 10, m$^2$ represents an integer from 0 to 2, r$^2$ and q$^2$ each represent an integer from 0 to 2, u$^2$ is an integer from 1 to 2, and p$^2$ represents 0 or 1, with the proviso that, when p$^2$ l$^2$, u$^2$ and r$^2$ each 1, q$^2$ is 0, A$^2$ is

D$^2$ is —CH$_2$— and X$^2$ is an oxygen atom, and R$^{40}$ and R$^{41}$ collectively have at least 3 carbon atoms.

12. The phthalocyanine compound of claim 11, wherein in formula (IV), q$^2$ is 0, r$^2$ is 1, and u$^2$ is 1 or 2.

13. The phthalocyanine compound of claim 12, wherein in formula (IV), A$^2$ is

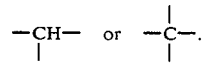

14. The phthalocyanine compound of claim 12, wherein in formula (IV), u$^2$ is 1, l$^2$ is other than 0, A$^2$ is

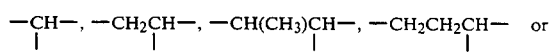

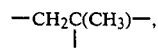

and D$^2$ is —U$^4$—(CH$_2$)$_b$—, —V$^4$—[CH(CH$_3$CH$_2$]— or —W$^4$—[CH$_2$CH(CH$_3$)]— in which U$^4$, V$^4$ and W$^4$ each independently represent an oxygen or sulfur atom and b is an integer from 1 to 3.

15. The phthalocyanine of claim 11, wherein in formula (IV), q$^2$, u$^2$ and m$^2$ each are 1, r$^2$ is 0, A$^2$ is

B$^2$ is —U$^5$—(CH$_2$)$_c$—, —V$^5$—[CH(CH$_3$)CH$_2$]— or —W$^5$—[CH$_2$CH(CH$_3$)]—, in which U$^5$, V$^5$ and W$^5$ independently represent an oxygen or sulfur atom and c is an integer from 1 to 3, and D$^2$ is —C(R$^{42}$)H— in which R$^{42}$ represents a hydrogen atom or a methyl or ethyl group.

* * * * *

UNITED STATES PATENT AND TRADEMARK OFFICE
CERTIFICATE OF CORRECTION

PATENT NO. : 5,380,842
DATED : January 10, 1995
INVENTOR(S) : Hisato ITOH et al.

It is certified that error appears in the above-indentified patent and that said Letters Patent is hereby corrected as shown below:

Claim 1, Column 90, line 29: Change " $R^5$ " to read -- $R^3$ --.

Signed and Sealed this

Second Day of May, 1995

Attest:

BRUCE LEHMAN

Attesting Officer        Commissioner of Patents and Trademarks